US008426126B2

(12) United States Patent
Latham et al.

(10) Patent No.: US 8,426,126 B2
(45) Date of Patent: Apr. 23, 2013

(54) MODIFIED SURFACES AS SOLID SUPPORTS FOR NUCLEIC ACID PURIFICATION

(75) Inventors: Gary J. Latham, Austin, TX (US);
Xingwang Fang, Austin, TX (US);
Richard C. Conrad, Austin, TX (US);
Jon A. Kemppainen, Austin, TX (US);
Robert A. Setterquist, Austin, TX (US);
Brittan L. Pasloske, Austin, TX (US)

(73) Assignee: Applied Biosystems, LLC, Carlsbad, CA (US)

( * ) Notice: Subject to any disclaimer, the term of this patent is extended or adjusted under 35 U.S.C. 154(b) by 316 days.

(21) Appl. No.: 10/955,974

(22) Filed: Sep. 30, 2004

(65) Prior Publication Data

US 2005/0208510 A1 Sep. 22, 2005

Related U.S. Application Data

(60) Provisional application No. 60/554,278, filed on Mar. 18, 2004.

(51) Int. Cl.
*C12Q 1/68* (2006.01)
*C12P 19/34* (2006.01)

(52) U.S. Cl.
USPC ............................ 435/6.1; 435/6.11; 435/6.12

(58) Field of Classification Search ........................ None
See application file for complete search history.

(56) References Cited

U.S. PATENT DOCUMENTS

| | | | |
|---|---|---|---|
| 4,452,773 A | 6/1984 | Molday | 424/1.37 |
| 5,075,430 A | 12/1991 | Little | 536/25.41 |
| 5,234,809 A | 8/1993 | Boom et al. | 435/91.2 |
| 5,523,231 A | 6/1996 | Reeve | 435/270 |
| 5,545,522 A | 8/1996 | VanGelder et al. | 435/6 |
| 5,646,263 A * | 7/1997 | Ekenberg et al. | 536/25.4 |
| 5,681,946 A | 10/1997 | Reeve | 536/25.4 |
| 5,705,628 A * | 1/1998 | Hawkins | 536/25.4 |
| 5,753,477 A | 5/1998 | Chan | |
| 6,027,945 A | 2/2000 | Smith et al. | 436/526 |
| 6,084,091 A | 7/2000 | Müller et al. | |
| 6,664,379 B1 | 12/2003 | Kudlicki et al. | 530/387.9 |
| 7,700,744 B2 | 4/2010 | Elaissari et al. | 530/412 |
| 2002/0000398 A1 | 1/2002 | Skold | |
| 2004/0161788 A1 | 8/2004 | Chen et al. | 435/6 |
| 2005/0014169 A1 | 1/2005 | Latham et al. | 435/6 |
| 2005/0026284 A1 | 2/2005 | Kudlicki et al. | 435/455 |

FOREIGN PATENT DOCUMENTS

| | | |
|---|---|---|
| DE | 4333805 A1 | 3/1995 |
| EP | 0515484 B1 | 4/1995 |
| EP | 1 375 660 A1 | 5/2003 |
| JP | 2703114 | 1/1998 |
| JP | 2001252100 | 9/2001 |
| JP | 2003339379 | 12/2003 |
| WO | WO 96/09379 | 3/1996 |
| WO | WO 97/08547 | 3/1997 |
| WO | WO 99/30160 * | 6/1999 |
| WO | WO 99/58664 | 11/1999 |
| WO | WO 01/70831 A1 | 9/2001 |
| WO | WO 02/55727 A2 | 1/2002 |
| WO | WO 02/066993 A1 | 8/2002 |
| WO | WO 02/098364 | 12/2002 |
| WO | WO 02/103056 | 12/2002 |

OTHER PUBLICATIONS

Boom et al. Journal of Clinical Microbiology vol. 28:495-503. 1990.*
Gruttner et al. Journal of Magnetism and Magnetic Materials vol. 225:1-7. 2001.*
Chegel et al. Journal of Biochemical and Biophysical Methods vol. 50:201-216. Jan. 4, 2002.*
Boom et al., "Rapid and simple method for purification of nucleic acids," *J. Clin Microbiol*, 28(3):495-503, 1990.
Neilsen et al., "Sequence-selective recognition of DNA by strand displacement with a thymine-substituted polyamide," *Science*, 254(5037):1497-1500, 1991.
Vogelstein and Gillespie, "Preparative and analytical purification of DNA from agarose," *Proc. Natl. Acad. Sci.*, USA, 76:615-619, 1979.
Yamado et al., "A new method for extracting DNA or RNA for polymerase chain reaction," *J. Viral Methods*, 27:203-210, 1990.
U.S. Appl. No. 60/547,721, filed Feb. 25, 2004, Latham and Pasloske.
EPO Communication pursuant to Article 94(3) EPC mailed Jul. 17, 2008 for App No. 05760857.2-1222 entered into EP phase from PCT/US05/009189 entitled "Modified Surfaces as Solid Supports for Nucleic Acid Purification;" Inventors: G. Latham, X, Fang, R. Conrad, J. Kemppainen, R. Setterquist and B. Pasloske; Applicant: Ambion Inc.
EPO Communication pursuant to Article 94(3) EPC mailed Apr. 12, 2010 for App No. 05760857.2-1222 entered into EP phase from PCT/US05/009189 entitled "Modified Surfaces as Solid Supports for Nucleic Acid Purification;" Inventors: G. Latham, et al.; Applicant: Ambion Inc.
EPO Communication pursuant to Article 96(2) EPC mailed Apr. 12, 2007 for App No. 05760857.2-1222 entered into EP phase from PCT/US05/009189 entitled "Modified Surfaces as Solid Supports for Nucleic Acid Purification;" Inventors: Gary Latham, Xingwang Fang, Richard Conrad, Jon Kemppainen and Robert Setterquist; Applicant: Ambion Inc.
Written Opinion and Search Report mailed Sep. 15, 2005 for PCT/US05/009189 filed Mar. 18, 2005 entitled "Modified Surfaces as Solid Supports for Nucleic Acid Purification;" Inventors: Gary Latham, Xingwang Fang, Richard Conrad, Jon Kemppainen and Robert Setterquist; Applicant: Ambion Inc.
Boccuzzi et al., "Preparation of DNA extracted from enviromental water samples for PCR amplification", *Journal of Microbiological Methods*, vol. 31, Issue 3, Jan. 1998, 193-199.
Livore et al., "A Sepbadex column procedure for DNA isolation is also useful for detecting dsRNA", *Nucleic Acids Research*, vol. 16, No. 2, Jan. 25, 1988, 776.
Pederson, "Spin-col. Chromatography for DNA Purification", *Analytical Biochemistry*, vol. 239, No. 1, May 20, 2006, 117-118.

* cited by examiner

*Primary Examiner* — Young J Kim

(57) ABSTRACT

The invention relates to methods of separating polynucleotides, such as DNA, RNA and PNA, from solutions containing polynucleotides by reversibly binding the polynucleotides to a solid surface, such as a magnetic microparticle.

32 Claims, 6 Drawing Sheets

CD=Charcoal Dextran
ND-S=Nanomag® Dextran-SO3H
STD Curve=Standard curve drawn from serial dilutions of the input RNA stock that was not subject to bead purification CD=Charcoal Dextran
ND=Nanomag® Dextran
ND-S=Nanomag® Dextran-SO3H
IP=Isopropanol Solvent Used
EtOH=Ethanol Solvent Used

MODIFIED SURFACES AS SOLID SUPPORTS FOR NUCLEIC ACID PURIFICATION

CROSS REFERENCE TO RELATED APPLICATIONS

This application claims the benefit of U.S. Provisional Application Ser. No. 60/554,278, filed Mar. 18, 2004, the entire contents of which are specifically incorporated herein by reference.

BACKGROUND OF THE INVENTION

1. Field of the Invention

The present invention relates generally to the field of the purification of nucleic acids. In particular, it relates to the purification of nucleic acids, for example, RNA, DNA, and/or PNA using polymer-modified surfaces and/or resin-based surfaces.

2. Description of Related Art

Many molecular biological techniques such as reverse transcription, cloning, restriction analysis, and sequencing involve the processing or analysis of biological materials. The materials most commonly analyzed in this regard are polynucleotides such as RNA and DNA. These techniques generally require that such materials be substantially free of contaminants capable of interfering with such processing or analysis procedures. Such contaminants generally include substances that block or inhibit chemical reactions, (e.g., nucleic acid or protein hybridizations, enzymatically catalyzed reactions, and other types of reactions, used in molecular biological techniques), substances that catalyze the degradation or depolymerization of a nucleic acid or other biological material of interest, or substances that provide "background" indicative of the presence in a sample of a quantity of a biological target material of interest when the nucleic acid is not, in fact present in the sample. Contaminants also include macromolecular substances from the in vivo or in vitro medium from which a nucleic acid material of interest is isolated, macromolecular substances such as enzymes, other types of proteins, polysaccharides, or polynucleotides, as well as lower molecular weight substances, such as lipids, low molecular weight enzyme inhibitors or nucleotides or oligonucleotides. Contaminants can also be introduced into a target biological material from chemicals or other materials used to isolate the material from other substances. Common contaminants of this last type include trace metals, dyes, and organic solvents.

Obtaining polynucleotides sufficiently free of contaminants for molecular biological applications is complicated by the complex systems in which such polynucleotides are typically found. These systems, e.g., cells from tissues, cells from body fluids such as blood, lymph, milk, saliva, mucus, urine, feces, semen, or the like, cells in culture, agarose or polyacrylamide gels, or solutions in which target nucleic acid amplification has been carried out, typically include significant quantities of contaminants from which the polynucleotide(s) of interest must be isolated before being used in a molecular biological procedure.

A variety of techniques have been developed to allow for the purification of polynucleotides from contaminants. Some of these techniques involve adsorbing nucleic acids on glass or silica-gel particles in the presence of chaotropic salts is known (Vogelstein, and Gillespie, 1979). According to this method, using high concentrations of chaotropic salts, such as sodium iodide, sodium perchlorate, or guanidine thiocyanate, DNA is isolated and purified from agarose gels and RNA and DNA preparations are isolated and purified from various extracts (Boom et al. 1990; Yamado et al., 1990).

Although the physical processes resulting in an adsorption of the nucleic acids on mineral substrates in the presence of chaotropic reagents are not understood in detail, it is believed that the reason of this adsorption lies in disturbances of higher-order structures of the aqueous medium. This leads to adsorption or denaturation of the dissolved nucleic acid on the surface of the glass or silica-gel particles. In the presence of high concentrations of chaotropic salts, this adsorption will occur almost quantitatively. Elution of the adsorbed nucleic acids is performed in the presence of buffers having low ionic strengths (salt concentrations).

Prior methods allow for the isolation of nucleic acids and fragments thereof using glass, silica, zeolite, or diatomaceous earth (Little, U.S. Pat. No. 5,075,430; Boom, U.S. Pat. No. 5,234,809). These methods may be used in a form with filters or columns, or as magnetically responsive particles (hereinafter, "magnetic particles") to expedite separations. For example, (Smith, U.S. Pat. No. 6,027,945) teaches the purification of RNA and DNA from silica magnetic beads.

Silica magnetic particles have limited utility in some samples. For example, the inventors have found that silica beads cannot efficiently isolate RNA from certainly biosamples, such as human plasma. Thus there exists a need for other support chemistries that can bind and purify RNA in manner that is adaptable to streamlined procedures, particularly for automated high throughput sample preparation.

Hawkins (U.S. Pat. No. 5,705,628) teaches that carboxy-coated magnetic particles can be used to isolate DNA, but provides no examples or data supporting the use of such particles for the purification of RNA. Moreover, these particles are chemically distinct from dextran-modified particles, which do not contain carboxy groups.

Nargessi and Pourfarzaneh (U.S. patent application Publication 2003/0092045) appear to disclose the use of cellulose particles or cellulose paper in the isolation and purification of nucleic acids such as DNA, RNA, and PNA. A combination of PEG and NaCl is suggested to allow binding of the nucleic acids, which can then be purportedly eluted in water or TE buffer. However, the application provides no examples or data supporting the use of such particles for the purification of RNA. Additionally, the application appears to report the purification of DNA by Sephadex G-25, although no binding buffers other than those containing PEG and NaCl are described. The paper does not appear to teach or suggest anything about the purification of nucleic acids, and RNA in particular, using magnetic particles.

Long chain carbohydrate molecules have been used to precipitate nucleic acids. For example, Dextran and glycogen have been used as co-precipitants for DNA. Polyethyleneglycol (PEG), in combination with appropriate salt concentrations, induces nucleic acid precipitation. Moreover, PEG/salt conditions also enable DNA purification using carboxy-modified (U.S. Pat. No. 5,705,628) and cellulose particles (U.S. patent application Publication 2003/0092045).

Dextran describes a family of polysaccharides that are produced by bacteria when grown on a sucrose substrate. Dextran is a glucose polymer linked primarily by $\alpha(1 \rightarrow 6)$ bonds. A number of dextrans exist, and these are differentiated by the extent of branching and polymer chain length of the $\alpha$-D-glucopyranosyl monomers. Dextrans are distinguished by their average molecular weight; for example, Dextran 40 has an average molecular weight of 40,000, whereas Dextran 75 has an average molecular weight of 75,000. Historically, Dextran has been used in the food industry, and therapeutically as a plasma volume expander and blood flow adjuvant. Dextran has also found use for emerging clinical applications of magnetic microparticles; dextran is a preferred coating for such particles owing to its biocompatibility and biodegradability, and its abundance of chemical "handles" (hydroxyl groups) that can be functionalized with a range of different chemistries. In this application, the dextran-coated particles may be used as a magnetic carrier for target drug delivery. For example, Micromod Partikeltechnologie GmbH sells several dextran-modified particles that are 50 nm to 250 nm in size for purposes of drug targeting or MRI contrast imaging. Two of these particles (Nanomag® Dextran (plain) and Nanomag® Dextran-$SO_3H$) are described herein in the context of the invention. Advanced Magnetics, Inc., offers a Dextran-modified magnetic particle termed Combidex® that has found utility as a localizing agent for the diagnostic imaging of lymph nodes.

In contrast, applications for dextran-modified particles, specifically magnetic dextran-modified particles, in nucleic acid purification from biosamples are lacking. Although a crosslinked dextran particle known as Sephadex (Amersham Biosciences) is currently used to purify DNA in various molecular biology protocols, this purification is accomplished by size exclusion in a non-organic, non-chaotropic solution that does not require specific binding interactions between DNA and the non-magnetic Sephadex particle itself. Indeed, the application of choice for Sephadex in DNA purification is to allow the facile separation of unincorporated ("free") deoxynucleotides from the target DNA polymer that is free from biological contaminants. No embodiments for the use of Sephadex exist for the efficient isolation of nucleic acid from biosamples.

Magnetic particles modified with PEG are commercially available. Micromod Partikeltechnologie GmbH sells several magnetic particles of various sizes that have been modified with PEG-300; that is, PEG polymers with an average molecular weight of 300 g/mol. However, there appears to be no prior use of these particles for nucleic acid purification.

In view of the above, there is a need for nucleic acid purification protocols that overcome some or all of the problems incumbent in the state of the art at the time of the filing of this application.

SUMMARY OF THE INVENTION

The present invention relates generally to the field of the purification of nucleic acids. In particular, it relates to the purification of nucleic acids, for example, RNA, DNA, and/or PNA using polymer-modified surfaces and/or resin-based surfaces.

In some general embodiments, the invention relates to methods of reversibly binding at least one polynucleotide to one or more surface comprising a polymer or resin, comprising: contacting the surface with a solution containing at least one polynucleotide; and adjusting a salt concentration and/or an organic solvent concentration of the solution to allow for binding of the polynucleotide onto the surface.

More specific embodiments relating to the use of polymers include methods of reversibly binding at least one polynucleotide to one or more surface comprising a polymer, comprising: contacting the surface with a solution containing at least one polynucleotide; and adjusting a salt concentration and/or an organic solvent concentration of the solution to allow for binding of the polynucleotide onto the surface. In some embodiments, if the surface comprises a polymer, the polymer is further defined as comprising a polyvinylpyrrolidone, a polyethylene glycol, or a polymeric polyol. In some embodiments, any polymeric polyol cannot be cellulose.

In some preferred embodiments, the polymer is a polymeric polyol. In the context of this invention, the term "polymeric polyol" means a compound containing at least ten monomers of a triose, tetrose, pentose, hexose, or heptose. Preferred polymeric polyols include, but are not limited to: Dextran, for example any of the Dextrans described herein or known to those of skill, and polysaccharides, for example but not limited to xanthum gum, glycogen, ficoll, gum arabic, carageenan, amylose, agar, amylopectin, a xylan, or a beta-glucan. Of course, those of skill will be able to determine any number of polysaccharides, Dextrans, or other polymeric polyols that will work in the context of the invention by following the teachings of this specification. Other preferred polymers include polyethylene glycols, such as those described herein. Further, the polymers can be a polyvinylpyrrolidone (PVP), such as, but not limited to, those disclosed herein.

There are a variety of functional characteristics of polymers that, in some embodiments of the invention, indicate utility. For example, in some embodiments, the polymer is hydrophilic. Further, in the context of the invention, it is beneficial if the polymer binds to the polynucleotides in the solution at an acceptable level. For example, in some embodiments, the polymer will bind to at least 10%, 20%, 30%, 40%, 50%, 60%, 70%, 75%, 80%, 85%, 90%, 95%, 96%, 97%, 98%, 99%, or substantially 100% of the polynucleotides in the solution. Of course, this degree of binding may also be described as a range between and including any two of these percentages. Additionally, the polymer may, in some embodiments, be further defined as a polymer that will co-precipitate with nucleic acid in solution. In the context of this aspect of the invention, "co-precipitant" means any chemical capable of enhancing the precipitation of nucleic acid in solution.

In some preferred embodiments, the surface is on one or more magnetic particles, such as one or more magnetic microparticles. The use of such magnetic particles can facilitate separation of the bound polynucleotides from the solution.

In other embodiments, the salt concentration can be a concentration of one or more salts, including but not limited to sodium chloride, magnesium chloride, calcium chloride, potassium chloride, lithium chloride, barium chloride, cesium chloride, sodium perchlorate, guanidinium isothiocyanate, guanidinium hydrochloride, potassium iodide, and sodium iodide. Of course, those of skill will be able to determine suitable salts for use in the invention. In some embodiments, the salt concentration is from 0.1M to 5M, more preferably, from 0.5M to 3M and even more preferably from 1M to 2.5M. The organic solvent concentration can be a concentration of one or more organic solvents, including but not limited to, a C1 to C5 alcohol, a polyethylene glycol, a dimethyl sulfoxide, or an acetone. The concentration of the organic solvent may, in some embodiments be adjusted to between about 20% and 50% of the solution, more preferably for some embodiments to between about 30% and 50%, and in some currently preferred embodiments to between about 30% and 40%. In some specific embodiments, the salt is guanidinium isothiocyanate, for example, guanidinium isothiocyanate at a concentration between about 0.5M and about 3.0M.

The polynucleotide can be any form of polynucleotide, including but not limited to a natural, synthetic and/or recombinant polynucleotide. The polynucleotide may be a bacterial polynucleotide or a eukaryotic polynucleotide or a viral polynucleotide or a polynucleotide encoding a viral component. The polynucleotide can be a reaction product of DNA polymerization. The polynucleotide can be a DNA, such as a cDNA, genomic DNA, or synthetic DNA. The polynucleotide can be an RNA. In some embodiments, the conditions of the methods can be adjusted to allow for the recovery of small RNAs, such as RNAs of less than or equal to 100 bases in length. Specific examples of such small RNAs include siRNAs and/or miRNAs. The RNA can also be an amplified RNA.

Some embodiments of the invention further comprise preparing the solution. For example, preparing the solution may comprise performing an RNA amplification reaction, an in vitro transcription reaction, a reverse transcription reaction, a second strand DNA synthesis reaction, a DNase reaction, and/or or a PCR reaction. Preparing the solution may also comprise lysing a cell. In some further embodiments, preparing the solution comprises conjugating RNA, DNA, or PNA in the solution to a reporter dye.

In some specific embodiments of the invention, the methods are further defined as methods of isolating or concentrating RNA, DNA, or PNA. For example these methods may relate to methods of isolating or concentrating DNA, for example but not limited to genomic DNA. The methods may be further defined as methods of isolating or concentrating PCR products. The methods may be further defined as methods of isolating or concentrating RNA, for example but not limited to methods of isolating or concentrating cellular total RNA. The invention can relate to methods of isolating or concentrating viral and/or bacterial RNA and/or DNA. The invention may be further defined as directed to methods of isolating or concentrating amplified RNA. It is possible to use the methods of the invention to isolate or concentrate RNA containing non-standard nucleotides, that is, nucleotides modified from their naturally-occurring form in one or more ways.

It is further possible to conjugate the polynucleotides, for example RNA, DNA, or PNAs, to a reporter dye prior to the isolation or concentration thereof. One can fragment such RNA, DNA, or PNA and then hybridize at least a portion of the fragmented RNA, DNA, or PNA to a microarray. Of course, in some embodiments, it is not required to fragment prior to hybridizing at least a portion of the RNA, DNA, or PNA to a microarray.

In some embodiments, the invention relates to methods of separating at least one polynucleotide from a solution containing the polynucleotide, comprising: admixing at least one surface comprising a polymer and a solution containing at least one polynucleotide to produce an admixture, wherein the surface is further defined as comprising a polyvinylpyrrolidone, a polyethyleneglycol or a polymeric polyol, with the proviso that any polymeric polyol cannot be cellulose; adjusting a salt concentration and an organic solvent concentration of the admixture to concentrations wherein the at least one polynucleotide binds to the at least one surface; separating the at least one modified surface from the remainder of the admixture while the at least one polynucleotide is bound to the surface; and contacting the surface with an elution buffer, thereby separating the at least one polynucleotide from the at least one surface. In some preferred embodiments, the polymer is a polymeric polyol, a Dextran, a polysaccharide, a polymer that binds at least 10% of the polynucleotides in the solution, and/or a polymer that will co-precipitate with nucleic acid, as defined above. In preferred embodiments of this aspect of the invention, the surface is on a magnetic particle, such as a microparticle and the separation of the surface can be or is performed using a magnet. In more specific embodiments, at least one polynucleotide bound to the at least one surface is washed with a buffer solution that dissolves one or more impurities bound to the surface while leaving the at least one polynucleotide bound to the at least one surface. The at least one polynucleotide can, for example, be further defined as at least one RNA. The methods may even more specifically comprise binding the at least one RNA bound to the at least one surface in a method comprising using a selective binding solution that does not allow substantial DNA binding to the surfaces but does allow RNA binding to the surface. In some such embodiments, the RNA bound to the surfaces can be washed with a selective wash solution, wherein the selective binding solution substantially dissolves DNA fragments bound to the surfaces while leaving RNA fragments substantially bound to the surfaces. Alternatively, the practice of the method can result in at least one RNA bound to the at least one surface being eluted with a selective elution solution that elutes the at least one RNA fragment from the surface while leaving DNA fragments substantially bound to the surface. In some embodiments, the at least one polynucleotide is digested by one or more enzymes while bound to the at least one support. The polynucleotide may be any of the types of polynucleotides described above or below in this specification and/or known to those of skill in the art. Likewise, the solution may be any of the solutions described above or below in the specification and/or known to those of skill in the art. These methods may further be defined as methods of isolating or concentrating polynucleotides as described herein. The methods may also comprise preparing the solution as described above, which preparation may comprise lysing a cell.

In some embodiments of the invention, conditions for binding and washing the bound polynucleotides can be adjusted to allow for the preferential recovery of, e.g., RNA at the exclusion of DNA. This capability is important in some protocols as contaminating DNA can confound interpretations of RNA analyses in downstream reactions such as reverse transcription-PCR™ (RT-PCR). In this regard, the invention relates to embodiments wherein at least one RNA bound to at least one polymer-modified surface is comprised in a selective binding solution that does not allow substantial DNA binding to the polymer-modified surfaces but does allow RNA binding to the polymer-modified surface. Other specific embodiments involve washing RNA bound to the polymer-modified surfaces with a selective wash solution, wherein the selective binding solution substantially dissolves DNA fragments bound to the polymer-modified surfaces while leaving RNA fragments substantially bound to the polymer-modified surfaces. Further, at least one RNA bound to the at least one polymer-modified surface can be eluted with a selective elution solution that elutes the at least one RNA fragment from the polymer-modified surface while leaving DNA fragments substantially bound to the polymer-modified surface.

The methods described throughout this document can be used for the purification of RNA or DNA from a wide variety of sources. For example, the polynucleotide may be comprised in a solution further defined as a biosample, tissue lysate, a blood sample, a blood fraction, an in vitro transcription reaction, a reverse transcription reaction, a second strand DNA synthesis reaction, a DNase reaction, or a PCR reaction. Of course, this list is not exhaustive. Additionally, polynucleotides that are eluted from the polymer particles are suitable for a number of subsequent enzymatic reactions, including, but not limited to, nucleic acid amplification. Biochemical reactions may also be performed on the polynucleotides while they are still bound to the polymer microparticles.

Because the methods of the present invention can purify both RNA, which is single-stranded by definition, and double-stranded DNA, and, further, both small and large nucleic acid fragments, the invention has applicability in essentially any context in which polynucleotide separation is desired. In addition, the instant invention permits the standardization of manipulations and isolation carried out with polynucleotides. The present methods simplify the isolation of RNA from tissue lysates by allowing facile purification that is not limited by, e.g., larger tissue particulates that can impede the flow of solutions through the glass filter, in the case of the currently used method. The present methods also have the advantage of being able to purify RNA from human blood or blood fractions, whereas the currently available silica beads may be unsuitable for such. The present methods also have the advantage of being fast, thus allowing for the rapid throughput in isolating polynucleotides, low cost and simple to perform and produce high yields of polynucleotides. The present methods further have the advantage of allowing one to purify polynucleotides that are substantially free from impurities, such as a metals, contaminating proteins or other undesirable biomolecules, and organic solvents or salts that can interfere with the analysis or enzymatic manipulation of the polynucleotides. The present methods allow more efficient purification of modified RNA, such as that modified with amino allyl, biotin, cyanine dyes, or other reporter chemistries. Such modified RNA is often more difficult to purify using conventional approaches owing to the change in chemical properties of the RNA conferred by said modifications. These properties, coupled with its applicability to many procedures useful in molecular biology, make the methods particularly suitable for automation.

Other aspects of the invention relate to methods of reversibly binding at least one polynucleotide to one or more surface comprising a polymer, comprising: contacting the surface with a solution containing at least one polynucleotide; and adjusting a salt concentration and/or a concentration of a non-polyethelyene glycol nucleic acid coprecipitant in the solution to allow for binding of the polynucleotide onto the surface; wherein the polymer is further defined as comprising a polyvinylpyrrolidone, a polyethylene glycol, or a polymeric polyol, with the proviso that any polymeric polyol cannot be cellulose. Exemplary non-polyethelyene glycol nucleic acid co-precipitants include: PVP, ficoll, and/or gum arabic.

The invention also relates to kits for practicing the invention. Such kits may comprise one or more of: a binding buffer or one or more components thereof and at least one polymer-modified surface. The binding buffer comprises a suitable salt and a suitable organic solvent at concentrations suitable for binding polynucleotides to the surface of the surface during use, as described above. The binding buffer may also comprise a carrier compound such as poly(A) or poly(C) RNA, tRNA, or yeast RNA. The polymer-modified surface may be further defined as comprising a polyvinylpyrrolidone, a polyethyleneglycol, or a polymeric polyol, and in some embodiments, any polymeric polyol will not be cellulose. Kits of the invention may further comprise an elution buffer or one or more components thereof, wherein the elution buffer is capable of dissolving polynucleotides bound to the surface during use. The kits may further comprise a wash buffer or one or more components thereof, wherein the wash buffer is capable of dissolving impurities bound to the surface but is incapable of dissolving selective polynucleotides bound to the surface during use. In some aspects, purification of nucleic acid in the absence of organic reagents is desirable. As a result, kits may also include salt and a non-organic component, such as Ficoll, PVP, and/or other nucleic acid co-precipitants as described below.

In other embodiment, the kits may comprise a reagent or one or more components thereof that preserve the intactness of RNA or DNA during use. Such reagents may include but not be limited to those discussed throughout this document. Kits may also comprise specialized containers for sample collection, such as a vacuum tube for blood collection, and/or multiwell plates or tubes for sample processing. The kits may comprise reagents necessary for nucleic acid amplification, including PCR, RT-PCR, and/or RNA amplification (U.S. Pat. No. 5,545,522). Such kits may include enzymes such as DNA polymerase, reverse transcriptase, RNase H, DNase, and/or and RNA polymerase with the appropriate buffers and cofactors (such as metal ions and nucleotides/deoxynucleotides). The invention may be used in conjunction with nucleic acid amplification to allow the separation RNA or DNA from other components in the reaction after RNA or DNA polymerization. In addition, purification may be desirable after labeling reactions, whereby the nucleic acid is modified with a reporter dye and separation of the uncoupled dye and the dye-coupled RNA or DNA is desired.

Kits may also comprise a mixture of different types of surfaces chemistries. For example, more efficient DNA or RNA purification may be possible by combining two matrices which each bind DNA or RNA, respectively. Alternatively, particles that individually bind RNA can be combined with particles that bind DNA to allow the purification of total nucleic acid, in a single tube.

The kits of the present invention may be adaptable by the end-user to control whether, during use, the kit serves to isolate RNA only, DNA only, or RNA and DNA together. For example, by using appropriate dilution techniques, an end-user might dilute a stock elution or wash solution to a concentration where its use resulted in the isolation of both DNA and RNA, or to a concentration where it would be selective for RNA isolation.

Another aspect of the present invention is directed towards a method of reversibly binding at least one polynucleotide to one or more surfaces comprising a resin, comprising: contacting the surface with a solution containing at least one polynucleotide and adjusting a salt concentration and/or an organic solvent concentration of the solution to allow for binding of the polynucleotide onto the resin. Non limiting examples of resins include isocyanate, glycerol(Diol), piperidino-methyl, polyDMAP, DIPAM, aminomethyl, polystyrene aldehyde, Tris(2-aminomethyl) amine, morpholino-methyl, BOBA, triphenyl-phosphine, or benzylthio-methyl. In specific aspects, the resin is phenylsepharose, glycerol(diol), morpholino-methyl, piperidino-methyl, or polystyrene aldehyde. These and other resins discussed throughout this document and those known in the art are contemplated as being useful with the present invention. Similarly, the salt concentration, polynucleotides and conjugated polynucleotides, and solutions discussed above and throughout the present document are also contemplated as being useful with this aspect of the present invention.

Similar to the polymers of the present invention, there are a variety of functional characteristics of resins that, in some embodiments of the invention, indicate utility. It is beneficial if the resin binds to the polynucleotides in the solution at an acceptable level. The levels discussed above and throughout this document are contemplated. For example, such levels include the resin binding to at least 10%, 20%, 30%, 40%, 50%, 60%, 70%, 75%, 80%, 85%, 90%, 95%, 96%, 97%, 98%, 99%, or substantially 100% of the polynucleotides in the solution. Additionally, the resin may, in some embodiments, be further defined as a resin that will co-precipitate with nucleic acid in solution.

Another aspect of the present invention provides for a method of separating at least one polynucleotide from a solution containing the polynucleotide, comprising: admixing at least one surface comprising a resin and a solution containing at least one polynucleotide to produce an admixture; adjusting a salt concentration and an organic solvent concentration of the admixture to concentrations wherein the at least one polynucleotide binds to the at least one surface; separating the at least one surface from the remainder of the admixture while the at least one polynucleotide is bound to the surface; and contacting the surface with an elution buffer, thereby separating the at least one polynucleotide from the at least one surface. The resins, polynucleotides and conjugated polynucleotides, salts and corresponding salt concentrations, and solutions discussed above and throughout this document are contemplated as being useful with this aspect of the present invention. For example, the resin can be isocyanate, glycerol (Diol), piperidino-methyl, polyDMAP, DIPAM, aminomethyl, polystyrene aldehyde, Tris(2-aminomethyl)amine, morpholino-methyl, BOBA, triphenyl-phosphine, or benzylthio-methyl.

The kits of the present invention may also comprise one or more of: a binding buffer or one or more components thereof and at least one resin-modified surface. Such kits can also include an elution buffer or one or more components thereof, a wash buffer or one or more components thereof, and/or a reagent or one or more components thereof that preserve the intactness of RNA or DNA during use. The kits can also include the additional elements discussed above. The binding buffers, resins, elution buffers, wash buffers, reagents, and additional elements discussed above and throughout this document are contemplated as being useful with this aspect of the present invention.

It is contemplated that any embodiment discussed in this specification can be implemented with respect to any method, kit, reagent, or composition of the invention, and vice versa. Furthermore, compositions of the invention can be used to achieve methods of the invention.

The use of the word "a" or "an" when used in conjunction with the term "comprising" in the claims and/or the specification may mean "one," but it is also consistent with the meaning of "one or more," "at least one," and "one or more than one."

Throughout this application, the term "about" is used to indicate that a value includes the inherent variation of error for the device, the method being employed to determine the value, or the variation that exists among the study subjects.

The use of the term "or" in the claims is used to mean "and/or" unless explicitly indicated to refer to alternatives only or the alternatives are mutually exclusive, although the disclosure supports a definition that refers to only alternatives and "and/or."

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

DETAILED DESCRIPTION OF THE INVENTION

Figure 1:
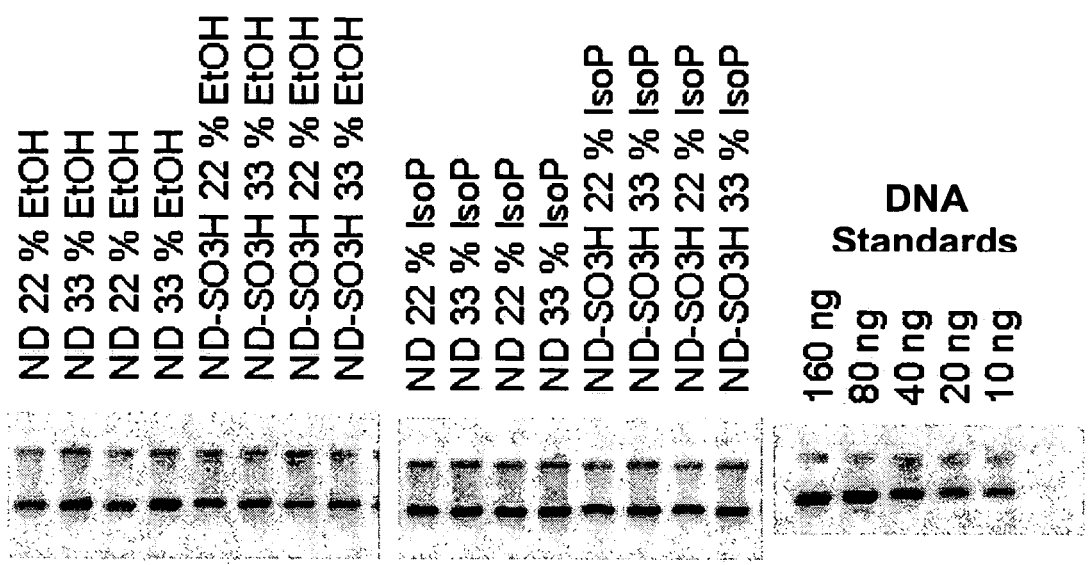
FIG. 1 Recovery of genomic lambda DNA using Dextran magnetic particles.
Figure 2:
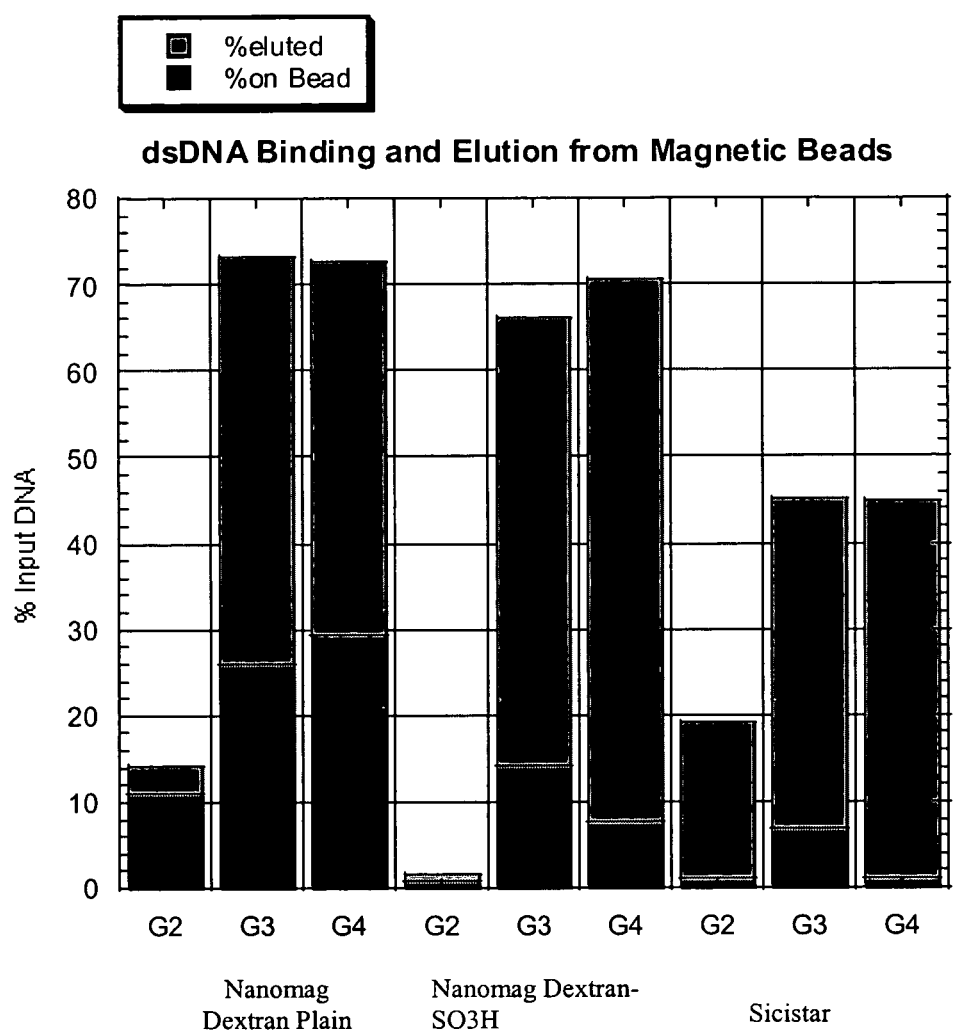
FIG. 2 Purification of an 830 base pair PCR™ product using Dextran magnetic particles.

Polynucleotides bind reversibly to a variety of polymer and/or resin-coated solid surfaces, such as polyvinylpyrrolidone, polyethylene glycol, or polymeric polyol coated surfaces. This binding can be exploited to allow for methods for convenient and rapid separation of polynucleotides, such as DNAs, RNAs, and/or PNAs, from solutions containing the polynucleotides and other biomolecules, such as proteins, monosaccharides, polysaccharides, lipids, free nucleotides, and RNA and from cellular components, such as cell membranes, is available. The invention also provides methods for purifying RNA that is substantially free from DNA.

A. Polymers, Resins, and Coated Surfaces

Polymer-modified solid surfaces and/or resin-modified solid surfaces which bind RNA or DNA and have sufficient surface area to permit efficient binding can be used in the present invention. Microparticles, fibers, beads and supports contain suitable surfaces. In some specific embodiments of the invention, magnetic microparticles are used. As used herein, "magnetic microparticles" are magnetically responsive microparticles which are attracted by a magnetic field. The magnetic microparticles used in the methods of the present invention comprise a magnetic metal oxide core, which is generally surrounded by a polymer coat which creates a surface that can bind to DNA, RNA, or PNA. The magnetic metal oxide core is preferably iron oxide, wherein iron is a mixture of $Fe^{2+}$ and $Fe^{3+}$. The preferred $Fe^{2+}/Fe^{3+}$ ratio is preferably 2/1, but can vary from about 0.5/1 to about 4/1.

1. Dextran and Dextran-Modified Surfaces

A "Dextran-modified surface" is a particle, microparticle, bead, magnetic bead, resin, or any particulate that comprises Dextran.

Suitable Dextran polymers include polymers of approximate molecular weight from 1,000 to about 410,000, or preferably from about 25,000 to about 100,000. The preparation of Dextran magnetic microparticles is described in U.S. Pat. No. 4,452,773, the teachings of which are hereby incorporated by reference into this application in their entirety. Unmodified magnetic microparticles comprising an iron oxide core (such as BioMag® Iron Oxide particles available from Polysciences, Inc., catalog # 84200-10) can also be used in the methods of the present invention.

It may be advantageous to further modify the Dextran microparticles with a functional group, such as an amine, carboxylate, sulfonate, trimethylamine, epoxide, or other group. As used herein, the term "functional group" refers to a Dextran-modified surface which is coated with moieties which each have a free functional group which is bound to the hydroxyl group or to a chemical spacer bound to the hydroxyl group of Dextran on the surface of the microparticle; as a result, the surfaces of the microparticles are coated with the functional group containing said moieties. The functional group may acts as a bioaffinity absorbent for the DNA, RNA, or PNA in solution. In one embodiment, the functional group is a sulfonic acid. This functional group has the potential advantage of allowing binding in low pH to maximize binding (when the sulfonate is protonated), but then allow a "charge-switch" by eluting the polynucleotide at a pH much above the pKa for the sulfonate. This charge-switch creates a "hard" negative charge on the surface of the support, which can help to expel the negatively charged polynucleotide and permit improved recoveries of polynucleotides.

The importance of having functional groups coat the surface of Dextran microparticles is demonstrated by the observation that improved yields of some nucleic acids are observed with Dextran sulfonate versus plain Dextran supports. The advantage of having a metal oxide core is illustrated by the observation that magnetic separations facilitate practice of the invention. Microparticles with an iron oxide core, which are commercially available from Polysciences, Inc. (catalog #84200-10) did not bind RNA in the methods of the present invention as it is described herein.

In the case where magnetic microparticles are used, said particles can be a variety of shapes, which can be regular or irregular; preferably the shape maximizes the surface areas of the microparticles. The magnetic microparticles should be of such a size that their separation from solution, for example by filtration or magnetic separation, is not difficult. In addition, the magnetic microparticles should not be so large that surface area is minimized or that they are not suitable for microscale operations. Suitable sizes range from about 0.1 micron mean diameter to about 100 micron mean diameter. A preferred size is about 0.25 to 1.0 micron mean diameter.

Suitable magnetic microparticles are commercially available. For example, in the Examples presented below, multiple forms of chemically distinct magnetic beads comprising Dextran were shown to bind and purify polynucleotides. These included: 1) Nanomag® Dextran (ND); 2) Nanomag® Dextran-SO3H (ND-SO3H); 3) BioMag® Dextran-Coated Charcoal; and 4) BioMag® Plus Dextran. Each is defined by chemical and physical specifications further below. A custom Dextran-coated bead was commissioned from Polysciences, Inc., that was a comparably useful support for nucleic acid purification. Some of these Dextran particles are described in greater detail below. However, the invention is in no way limited to these specific particles.

Nanomag® Dextran (Plain) (also referred to as "ND") is supplied by Micromod as Product No.: 09-00-252, and Product Name: Nanomag®-D. It has a plain surface, a size of 250 nm, a solid content of 25 mg/ml, a polydispersity index: <0.2, a cluster-typed shape, a density of 4.0 g/ccm, a magnetization of 43 emu/g particles (H=1000 Oe), and a saturation magnetization: >67 emu/g particles (H>10.000 Oe). It is stable in aqueous buffers of pH >4, but not in organic solvents or acidic solutions of pH <4. It is provided in the form of an aqueous suspension of 7.5*10E11 particles per ml and 3.1*10 E10 particles per mg. The product can be stored at 4° C. for at least 6 months. In some cases, the product is first centrifuged at 836×g for 20 min to remove the least magnetic responsive particles, and 0.05% sodium azide is added as a preservative. If treated in this way, the particles are typically supplied at a concentration of 10 mg/ml.

Nanomag® Dextran-SO3H is supplied by Micromod as Product No.: 09-09-252, and Product Name: Nanomag®-D (SO3H). It has an SO3H surface, a size of 250 nm, a solid content of 25 mg/ml, a polydispersity index: <0.2, a cluster-typed shape, a density of 4.0 g/ccm, a magnetization of 43 emu/g particles (H=1000 Oe), and a saturation magnetization: >67 emu/g particles (H>10.000 Oe). It is stable in aqueous buffers of pH >4, but not in organic solvents or acidic solutions of pH <4. It is provided in the form of an aqueous suspension of 3.0*10E11 particles per ml and 3.1*10E10 particles per mg. The product can be stored at 4° C. for at least 6 months.

BioMag® Dextran-Coated Charcoal is supplied by Polysciences, Inc., under Catalog #: 84510E. BioMag Dextran-Coated Charcoal is a suspension of BioMag particles approximately 1 µm in size which are covalently attached to Norit activated carbon and Dextran. The suspension is supplied in distilled water with 0.1% sodium azide added as a preservative. Each lot of BioMag Dextran-Coated Charcoal includes a total of 5 mg of BioMag and Dextran-coated charcoal per mL of particle slurry.

BioMag® Plus Dextran is supplied by Polysciences as a custom synthesis. This particle is a suspension of BioMag particles approximately 0.5-1 µm in size to which Dextran-40 (Amersham) is attached. The suspension is supplied in distilled water at a concentration of 50 mg/ml.

Of course, those of skill in the art, employing the teachings of this specification and the protocols taught herein, will be able to obtain and test, without undue experimentation, any number of Dextran compositions for suitability in the invention.

2. Polyethylene Glycol and Polyethylene Glycol-Modified Surfaces

Polyethylene Glycol (PEG) and PEG-modified surfaces are used to purify polynucleotides in some embodiments of the invention. A "PEG-modified surface" is a particle, microparticle, bead, magnetic bead, resin, or any particulate that comprises PEG.

PEG is a water-soluble organic used for the preparation of emulsifying agents, plasticizers and textile lubricants. PEG is also used as a fusogen to create hybridomas for monoclonal antibody production and as a bulking agent that can improve the efficiency of some enzymatic reactions. PEG is a polymeric form of the monomer ethylene glycol, with a formula of $(CH_2O)_n$, where n can be any of a large number of repeats. For example, n can be 10 to 100,000. Some embodiments of the invention will use PEG with n of 10, 20, 30, 40, 50, 100, 150, 200, 250, 300, 350, 400, 450, 500, 550, 600, 650, 700, 750, 800, 850, 900, 950, 1,000, 1,250, 1,500, 1,750, 2,000, 2,500, 3,000, 3,500, 4,000, 4,500, 5,000, 5,500, 6,000, 6,500, 7,000, 7,500, 8,000, 8,500, 9,000, 9,500, 10,000, 11,000, 12,000, 12,500, 15,000, 16,000, 17,000, 17,500, 18,000, 19,000, 20,000, 25,000, 30,000, 40,000, 50,000, 60,000, 70,000, 80,000, 90,000, 100,000 or more, or where n is any integer between any of these points, or n is within any range derivable between any two of these points.

Many forms of PEG are commercially available. For example, Sigma sells PEG-200, PEG-300, PEG-400, PEG-600, PEG-l000, PEG-1300-1600, PEG-1450, PEG-3000-3700, PEG-3500, PEG-6000, PEG-8000, and PEG-17500. Further, those of skill can obtain additional forms of PEG.

Suitable magnetic microparticles comprising PEG are commercially available. For example, Nanomag® PEG-300 (Plain) is supplied by Micromod as Product No.: 09-54-252, and Product Name: Nanomag®-D. It has a PEG-300 surface, a size of 250 nm, a solid content of 10 mg/ml, a polydispersity index: <0.2, a cluster-typed shape, a density of 4.0 g/ccm, a magnetization of 43 emu/g particles (H=1000 Oe), and a saturation magnetization: >67 emu/g particles (H>10.000 Oe). It is stable in aqueous buffers of pH >4, but not in organic solvents or acidic solutions of pH <4. It is provided in the form of an aqueous suspension of 3.0*10E11 particles per ml and 3.1*10E10 particles per mg. The product can be stored at 4° C. for at least 6 months.

Of course, those of skill in the art, employing the teachings of this specification and the protocols taught herein, will be able to obtain and test, without undue experimentation, any number of PEG compositions for suitability in the invention.

3. Polyvinylpyrrolidone and Polyvinylpyrrolidone-Modified Surfaces

Polyvinylpyrrolidone (PVP) and PVP-modified surfaces are used to purify polynucleotides is some embodiments of the invention. A "PVP-modified surface" is a particle, microparticle, bead, magnetic bead, resin, or any particulate that comprises PVP.

PVP is used in nucleic acid hybridization solutions, such as Denhardt's solution, and is included in some nucleic acid extraction protocols, particularly those that aim to isolate nucleic acids from plants. PVP complexes with phenolics and alkaloids can be used to remove these undesirable contaminates during sample preparation in advance of various molecular biological applications. PVP is made from the monomer n-vinyl pyrrolidone and is readily available at various molecular weights from chemical suppliers. For example, Sigma sells 10K, 40K, 360K molecular weight PVP formulations (Sigma), along with many others.

Of course, those of skill in the art, employing the teachings of this specification and the protocols taught herein, will be able to obtain and test, without undue experimentation, any number of PVP compositions for suitability in the invention.

4. Polysaccharide and Polysaccharide-Modified Surfaces

Polysaccharide and polysaccharide-modified surfaces are used to purify polynucleotides is some embodiments of the invention. A "Polysaccharide-modified surface" is a particle, microparticle, bead, magnetic bead, resin, or any particulate that comprises a polysaccharide.

Polysaccharides are based on a repeating sugar motif. This class of compounds is also known as polyols. These include dextran, ficoll, glycogen, gum arabic, xanthan gum, carageenan, amylose, agar, amylopectin, xylans, beta-glucans, and many others. Polymeric polysaccharides, such as glycogen or dextran, are used in nucleic acid precipitation reactions to improve the recovery of trace amounts of nucleic acids through co-precipitation with same. Any polymeric polyol that is an effective nucleic acid co-precipitant will have utility in purifying RNA or DNA when coupled to a solid support.

Of course, those of skill in the art, employing the teachings of this specification and the protocols taught herein, will be able to obtain and test, without undue experimentation, any number of polysaccharide compositions for suitability in the invention.

5. Chemical Resins and Chemical Resin-Modified Surfaces

Chemical resins and chemical resin-modified surfaces can be used to purify polynucleotides is some embodiments of the invention. Such resins include, but are not limited to isocyanate, glycerol, piperidino-methyl, polyDMAP (polymer-bound dimethyl 4-aminopyridine), DIPAM(Diisopropylaminomethyl, aminomethyl, polystyrene aldehyde, tris(2-aminomethyl) amine, morpholino-methyl, BOBA (3-Benzyloxybenzaldehyde), triphenyl-phosphine, and benzylthio-methyl. A "Resin-modified surface" is a particle, microparticle, bead, magnetic bead, resin, or any particulate that comprises a resin as described above.

Of course, those of skill in the art, employing the teachings of this specification and the protocols taught herein, will be able to obtain and test, without undue experimentation, any number of Dextran compositions for suitability in the invention.

B. Polynucleotides and Solutions Containing Polynucleotides

A "polynucleotide" can be DNA, RNA or a synthetic DNA analog such as a PNA (Nielsen et al., 1991).

A "solution containing polynucleotides" can be any aqueous solution, such as a solution containing DNA, RNA and/or PNAs. Such a solution can also contain other components, such as other biomolecules, inorganic compounds and organic compounds. The solution can contain DNA or RNA which is the reaction product of an amplification procedure. The solution may be derived from a biosample. A "biosample" as used herein, is a solution derived from biological matter, namely cells from tissues, cells from body fluids such as blood, saliva, lymph, milk, mucus, urine, feces, semen, or the like, or cells that are grown in culture. The target nucleic acid might also be DNA or RNA from virus particles that are contained within the biosample. The solution can also be a tissue lysate. A "lysate", as used herein, is a solution containing cells which contain polynucleotides and whose cell membranes have been disrupted, with the result that the contents of the cell, including the polynucleotides contained therein, are in the solution.

The solution can also be blood or a fraction of blood, such as plasma or serum. The polynucleotide in the solution with which the magnetic microparticles are combined can be RNA, DNA, and/or PNA. In addition, the polynucleotide can be homogeneous (i.e., polynucleotides which have the same nucleotide sequence). Alternatively, the polynucleotide can be heterogeneous, (i.e., polynucleotides of differing nucleotide sequences).

C. Separation of Polynucleotides from Solutions Containing Polynucleotides The following is a description of the present invention with reference to polynucleotides as exemplified by RNA and DNA. It is to be understood that the present invention is also useful for separation of PNAs in a similar manner.

As described above, binding polynucleotides to polymer-modified magnetic microparticles, either as is, or having a functional group-coated surface (e.g., a sulfonic acid group-coated surface) comprises adjusting the salt concentration and the concentration of organic solvent to a concentration of each suitable for binding polynucleotides reversibly onto the surface of the magnetic particles. Suitable salts may include guanidinium isothiocyanate (GITC), guanidinium hydrochloride, sodium chloride (NaCl), sodium perchlorate (NaClO$_4$), lithium chloride (LiCl), barium chloride (BaCl$_2$), potassium (KCl), calcium chloride (CaCl$_2$), magnesium chloride (MgCl$_2$) and cesium chloride (CeCl). Generally, GITC is used. Other solutes, such as urea and thiourea may be combined therein. Suitable organic solvents may include methanol, ethanol, propanol, butanol, pentanol, acetone, or dimethylsulfoxide. Preferred solvents are ethanol, propanol (isopropanol), and dimethylsulfoxide. A sufficient quantity of a salt and a sufficient concentration of organic solvent are combined with the combination of magnetic microparticles and polynucleotide-containing solution to produce a final salt concentration of from about 0.5M to about 2.0M and a final organic solvent concentration of from about 20% to about 50%. At appropriate concentrations of the two, polynucleotides bind to the surface of the Dextran microparticles. The binding of the polynucleotides to the magnetic microparticles is rapid; it is generally complete within 2 min or less.

Yields of RNA following elution in a low salt solution typically approach 100% when the magnetic microparticles are used in excess.

In one embodiment, the magnetic microparticles with bound polynucleotides are washed with a suitable wash buffer solution before separating the polynucleotides from the polymer microparticles by washing with an elution buffer. A suitable wash buffer solution has several characteristics and more than one type of wash buffer may be used. First, the wash buffer solution must have a sufficiently high concentration of salts and/or organic solvent such that the polynucleotides bound to the magnetic microparticles do not elute from of the microparticles, but remain bound to the microparticles. Suitable salt concentrations are about 0.5 M to 5.0 M, and preferably about 2 M, in the presence of preferably 20 to 50% organic solvent. A wash solution may also include organic solvent without salt, at concentrations are greater than about 50% and preferably about 80%. Second, the buffer solution is chosen so that impurities that are bound to the polynucleotides or microparticles are dissolved. The probability that this might occur is increased by using two wash solutions that differ in their composition. The pH and solute composition and concentration of the buffer solution can be varied according to the type of impurities which are expected to be present. The magnetic microparticles can be washed as often as required to remove the desired impurities. However, the number of washings is preferably limited to two or three in order to minimize loss of yield of the bound polynucleotide, and/or the particles themselves. When the microparticles are used in excess, RNA yields are typically 80% or greater after washing with a wash buffer and eluting with an elution buffer.

Temperature does not appear to be critical in the methods of separating DNA or RNA of the present invention. Ambient temperature is preferred, but any temperature above the freezing point of water and below the boiling point of water may be used.

Polynucleotide fragments of all sizes bind to magnetic microparticles at high ionic strength and at least 33% isopropanol. High ionic strength refers to salt concentrations greater than 0.5M. However, smaller fragments of DNA or RNA bind with lower affinity than large DNA fragments at lower ionic strengths, for example, about 0.5M salt concentration and lower and at least 33% isopropanol.

A further embodiment of the present invention is based on the discovery that the magnetic microparticles do not elute enzymes when the preferred methods for utility are used (Examples 12 and 15). The magnetic microparticles also do not inhibit the function of enzymes (Example 27). It is therefore possible to carry out biochemical reactions on DNA bound to the magnetic microparticles, e.g., by exposing the bound polynucleotide to enzymes capable of biochemically modifying the bound polynucleotide under conditions which cause the biochemical modification to take place. Preferably the biochemical reactions are carried out on purified bound polynucleotide (e.g., RNA of DNA bound to microparticles which have been separated from a lysate or from a solution in which a biochemical reaction such as PCR™ was carried out). The purified bound polynucleotide can also be washed with a suitable wash buffer. Because residual salt can inhibit the activity of certain enzymes, it is preferable that washings with high ionic strength salt solutions be followed with a washing with a lower ionic strength solution. The ionic strength of this solution should be low enough that enough residual salt is removed to prevent enzyme inhibition, but not so low that substantial losses in bound polynucleotide result. In some cases, the bound polynucleotides may be eluted to allow for more efficient enzyme-substrate interactions, wherein the residual polynucleotides can be readily rebound after said enzymatic reaction is complete. One specific example is the digestion of DNA using the enzyme DNase to remove DNA that may bind to the polymer microparticles along with RNA from a solution.

One embodiment of the present invention relates to methods of separating RNA from a solution containing RNA. This comprises a first step of reversibly binding RNA to a solid surface, such as magnetic microparticles whose surfaces are coated with polymer. In the method, the magnetic microparticles are combined with a solution containing RNA, after which the salt concentration and the organic solvent concentration of the resulting combination are adjusted to a concentration suitable for binding RNA onto the surface of the microparticles. In one embodiment, sufficient salt and organic solvent are added to the solution containing magnetic microparticle-bound RNA to result in a final concentration of from about 0.5M to about 5.0M salt and from about 20% to about 50% ethanol, isopropanol, acetone, or dimethylsulfoxide (DMSO). As a result, RNA is bound to the surfaces of the polymer magnetic microparticles. Subsequently, the magnetic microparticles in the resulting combination are separated from the supernatant. The magnetic microparticles having RNA bound thereto can, optionally, be washed with a suitable wash buffer before they are contacted with a suitable elution buffer, to elute and separate the RNA from the magnetic microparticles. In a final step, the polymer magnetic particles are separated from the elution buffer, which contains the polynucleotide, in solution. The magnetic microparticles are separated from the elution buffer by, for example, filtration or applying a magnetic field to draw down the microparticles.

D. Kits

Kits are also provided herein which contain some or all of the reagents necessary for separating polynucleotides, such as DNA, RNA and PNAs, from a solution containing polynucleotides by binding the polynucleotides to a polymer-modified and/or resin-modified solid surface that may or may not be magnetic in nature. Often, these kits will comprise non-magnetic or magnetic microparticles with a modified surface and a binding buffer. The binding buffer usually comprises a suitable salt and a suitable organic solvent which are both present at a concentration suitable for binding DNA to the surface of the magnetic microparticles. Alternatively, the organic solvent may not be included, but the user would be expected to provide it accordingly.

In one embodiment, the kits further comprise an elution buffer which is capable of dissolving the polynucleotide, such as RNA or DNA, bound to the polymer or resin microparticles. Such elution buffers are typically low ionic strength solutions, preferably with an ionic strength of 100 mM or less, or 50 mM or less, or most preferably, 15 mM or less. Such elution buffers may comprise water, 0.1 mM EDTA, and/or a combinations of 1-10 mM Tris (pH 7-9) and 0.1-1 mM EDTA. They might also include any other buffer, such as a GOOD's buffer, HEPES or any other buffer that can maintain a pH from about 7 to about 9. Other exemplary elution buffers may comprise a buffer, such as sodium citrate, that can maintain a pH from about 4 to 7. Alternatively, instead of a binding buffer and/or elution buffer, the kits can comprise the reagents for making the binding and/or elution buffer, to which a known amount of water can be added to create a binding and/or elution buffer of desired concentration. In addition, the kits may include a magnet apparatus to allow the separation of magnetic microparticles from solution.

In some embodiments, the kits further comprise a wash buffer that dissolves impurities bound to the microparticles, but does not result in elution of the polynucleotide bound to the microparticles. In terms of the invention, a "wash buffer" is any solution that is expected to preserve binding of the target nucleic acid while removing undesirable contaminants, such as protein, DNA, or salt during uses. A preferred wash buffer comprises 30-100% ethanol, isopropanol, or DMSO. A most preferred wash buffer is 70-90% ethanol. A key characteristic for a wash buffer is an ability to wash in a way that substantially maintains nucleic acid binding without high salt, since salt carryover to the eluent can potentially inhibit downstream reactions. Alternatively, instead of a wash buffer, the kit can comprise the reagents for making the wash buffer, to which a known amount of water can be added to create a wash buffer of desired concentration.

In yet another embodiment, the kits comprise the reagents necessary to create a lysate from an intact tissue. Such reagents may include GITC and/or a detergent that can both disrupt the tissue architecture and solubilize the intracellular contents as well as control cellular RNase activities that might otherwise threaten the intactness of RNA, if RNA is destined for purification using the invention. In this regard, any of the nuclease inhibitors disclosed in: (i) U.S. Provisional Application No. 60/547,721 entitled "Nuclease Inhibitors for Use In Biological Applications" by Latham et al., filed on Feb. 25, 2004; and (ii) U.S. application Ser. No. 10/786,875 entitled "Improved Nuclease Inhibitor Cocktail" by Latham et al., filed on Feb. 25, 2004, which is a continuation-in-part application of co-pending U.S. application Ser. No. 10/675,860 filed Sep. 30, 2003, which is a continuation of application Ser. No. 09/669,301 filed Sep. 25, 2000, now U.S. Pat. No. 6,664,379, which claims the benefit of U.S. Provisional Application No. 60/155,874, filed Sep. 24, 1999. The entire text of each of the foregoing applications is specifically incorporated herein by reference without disclaimer.

In yet another embodiment, the kits comprise the reagents necessary to preserve and/or extract RNA or DNA from biological fluids such as blood or blood fractions (plasma, serum, and/or white blood cells), saliva, lymph, milk, saliva, mucus, urine, feces, or semen. The RNA may be host or bacterial total RNA or Poly(A)-tailed RNA or viral RNA. The DNA may be host or bacterial total DNA, or viral DNA. Isolation of bacterial RNA or DNA or isolation of viral RNA or DNA may include the genetic elements that contribute to the following diseases: Human immunodeficiency syndrome, Herpes, Hepatitis, Influenza, Mononucleosis, Pneumonia, Genital Human Papilloma Virus Infection, Cancer, Foot and mouth disease, Swine vesicular disease, Peste des petits ruminants, Lumpy skin disease, Bluetongue, African horse sickness, Classical swine fever, Newcastle disease, Vesicular stomatitis, Rinderpest, Contagious bovine pleuropneumonia, Rift Valley fever, Sheep pox and goat pox, African swine fever, Avian chlamydiosis, Avian infectious bronchitis, Avian infectious laryngotracheitis, Avian mycoplasmosis (*M. gallisepticum*), Avian tuberculosis, Duck virus enteritis, Duck virus hepatitis, Fowl cholera, Fowl pox, Fowl typhoid, Infectious bursal disease (Gumboro disease), Marek's disease, Pullorum disease, Bovine anaplasmosis, Bovine babesiosis, Bovine brucellosis, Bovine cysticercosis, Bovine genital campylobacteriosis, Bovine tuberculosis, Bovine Viral Diarrhea, Dermatophilosis, Enzootic bovine leukosis, Haemorrhagic septicaemiae, Infectious bovine rhinotracheitis/infectious pustular vulvovaginitis, Malignant catarrhal fever, Highly pathogenic avian influenza, West Nile Virus Disease, Avian Leukosis, Swine Fever, Contagious equine metritis, Dourine, Epizootic lymphangitis, Equine encephalomyelitis (Eastern and Western), Equine infectious anemia, Equine influenza, Equine piroplasmosis, Equine rhinopneumonitis, Equine viral arteritis, Glanders, Horse mange, Horse pox, Japanese encephalitis, Surra (*Trypanosoma evansi*), Venezuelan equine encephalomyelitis, Leishmaniosis, Anthrax, Aujeszky's disease, Echinococcosis/hydatidosis, Heartwater, Leptospirosis, New world screwworm (*Cochliomyia hominivorax*), Old world screwworm (*Chrysomyia bezziana*), Paratuberculosis, Q fever, Rabies, Trichinellosis, Severe Acute Respiratory Syndrome (SARS)

In yet another embodiment, the kits comprise the reagents necessary for nucleic acid amplification, including PCR, RT-PCR, and/or RNA amplification (U.S. Pat. No. 5,545,522). Such kits may include enzymes such as DNA polymerase, reverse transcriptase, RNase H, DNase, and/or and RNA polymerase with the appropriate buffers and cofactors (such as metal ions and nucleotides/deoxynucleotides). The invention may be used in conjunction with nucleic acid amplification to allow the separation RNA or DNA from other components in the reaction after RNA or DNA polymerization. In addition, purification may be desirable after labeling reactions, whereby the nucleic acid is modified with a reporter dye and separation of the uncoupled dye and the dye-coupled RNA or DNA is desired.

An exemplary RNA amplification kit according to the invention may include one, more, or all of the following components: reverse transcriptase, first strand buffer, dNTP Mix, RNase inhibitor protein, T7 Oligo(dT) Primer, RNase H, second round primers, control RNA, second strand buffer, DNA Polymerase, cDNA binding magnetic beads, cDNA wash buffer, amplified RNA (aRNA) binding buffer, aRNA binding beads (Dextran), bead resuspension solution, aRNA wash solution, RNA fragmentation reagent, T7 RNA polymerase mix, T7 RNA polymerase buffer, elution solution, and nuclease-free water. These kits may include a variety of other components for more specialized embodiments, for example but not limited to, one or more: amino allyl nucleotide (such AA-UTP), biotinylated nucleotide (such as biotin UTP), Cy-modified nucleotide, free Cy dye, and/or DNase/DNase buffer. Further, while it is possible to use dextran magnetic beads for both cDNA and aRNA purification, one can use any of a variety of alternative magnetic beads and/or alternative separation strategies to separate either the cDNA or aRNA. Of course, some kits may comprise only a subset of these components, with one desiring to run the reaction obtaining components not within the kit as needed from other sources. Further, a given kit may comprise enough of one or more of the components to run one or multiple reactions.

The invention contemplates kits for the isolation of total RNA from a variety of sources. A total RNA isolation kit for isolation of RNA from cells or tissues, according to the invention may include one, more, or all of the following components: lysis/binding solution, RNA binding beads (for example Dextran-coated beads), bead resuspension solution, wash solution, elution solution, DNase I buffer, nuclease free water, a processing plate, and/or a processing plate lid. A viral RNA isolation kit, for isolation of viral RNA from, typically, plasma, serum, milk, etc., may include one, some, or all of the following components: viral RNA lysis/binding solution, carrier RNA, RNA binding beads, bead resuspension solution, one or more wash solution, nuclease free water, a processing plate, and/or a processing plate lid. Of course, some kits may comprise only a subset of these components, with one desiring to run the reaction obtaining components not within the kit as needed from other sources. Further, a given kit may comprise enough of one or more of the components to run one or multiple reactions.

Kits may also comprise a mixture of different types of surfaces chemistries. For example, more efficiently DNA or RNA purification may be possible by combining two matrices which each bind DNA or RNA, respectively. Alternatively, particles that individually bind RNA can be combined with particles that bind DNA to allow the purification of total nucleic acid, in a single tube.

The present invention will now be illustrated by the following examples, which are not limiting in any way.

EXAMPLES

The following examples are included to demonstrate preferred embodiments of the invention. It should be appreciated by those of skill in the art that the techniques disclosed in the examples which follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

The Yield and Intactness of RNA Purified from Dilute Solution using Dextran Magnetic Beads In a study demonstrating the ability of the Dextran particles to bind and elute RNA, a total of 10 µg of RNA (rat kidney total RNA, Ambion) was added to 250 µg of the magnetic beads in a well of a 96-well plate containing 50 µl of a 0.5× guanidinium isothiocyanate (GITC) lysis solution (Ambion) and 50 µl of 100% ethanol (thus, 50% ethanol final concentration). The solution was incubated at room temperature (23° C.) for 2-3 min, and then the binding buffer was removed after the particles were drawn to the side by contact of the plate with a conventional magnet (Magnetic Stand-96, Ambion). The bound RNA was eluted directly in 25 µl of RNase-free water (Ambion). The RNA yield was quantified by absorbance, using a NanoDrop spectrophotometer. The intactness of the RNA was assessed using the 2100 BioAnalyzer (Agilent) analysis software after separation on an RNA Labchip. The input RNA had a 28S/18S ratio of ~1.0. As shown in Table 1, 92% of the input RNA was recovered (25 µl of a solution containing 365 and 366 ng/µl, respectively). Furthermore, the integrity of the eluted RNA was equivalent to the input material. Thus intact RNA can be efficiently recovered from dilute solution using Dextran beads.

TABLE 1

RNA Yield and Intactness after Purification on Dextran-containing Particles.

| Nucleic Acid Support | RNA Yield | % Recovery | 28S/18S Ratio |
|---|---|---|---|
| Nanomag Dextran (ND) | 9.2 µg | 92 | 1.02 |
| Nanomag Dextran-SO3H (ND-SO3H) | 9.2 µg | 92 | 0.97 |

Example 2

RNA Binding Capacity of the Dextran Magnetic Beads

To demonstrate that Dextran particles could bind a large fraction of their mass in RNA, a binding capacity measurement was performed. First, 40 µl of 1% Nanomag Dextran or 100 µl of 2.5% Nanomag Dextran-SO3H beads were pre-washed 3 times in 1 ml of water or 0.5× GITC lysis buffer (Ambion). After the last wash, beads were resuspended in either wash of 0.5× GITC lysis buffer (Ambion) such that the final concentration of beads was 1%. Next, the 5 µl of the 1% bead slurry (50 µg) was added to a 100 µl solution containing 0.5× GITC lysis buffer (Ambion), 50% ethanol, and 10 µg of RNA (rat kidney total RNA, Ambion). Samples were incubated at room temperature for 2-3 min, and the magnetic particles pelleted with a conventional magnet (Magnetic Stand-96, Ambion). The residual binding buffer was then carefully removed by suction with a small aperture pipet tip. The RNA was eluted in 50 µl of RNase-free water (Ambion). As shown in Table 2, 6.7-7.1 µg (67-71%) of the input 10 µg total RNA could be eluted from the Dextran beads. Thus, the Nanomag Dextran and Nanomag Dextran-SO3H beads can bind at least 20% of their mass in RNA. Pre-washing the beads in either water or lysis buffer had no measurable impact on the efficiency of RNA recovery. The inventors have further demonstrated that a mass of RNA greater than the mass of the Dextran particles can be efficiently purified (Example 28).

TABLE 2

RNA Binding Capacity of Dextran Magnetic Beads

| RNA Yield | Bead Type | Pre-Wash |
|---|---|---|
| 6.7 µg | Nanomag Dextran | dH$_2$O |
| 6.7 µg | Nanomag Dextran | GITC |
| 7.1 µg | Nanomag Dextran-SO3H | dH$_2$O |
| 6.8 µg | Nanomag Dextran-SO3H | GITC |

Example 3

Purification of Genomic DNA using Dextran Particles

DNA, as well as RNA, can be purified using Dextran particles such as the ones described here. To evaluate the binding and elution of double-stranded DNA (dsDNA), the following study was performed. A total of 5 µl of 1% ND or ND-SO3H beads were combined with 100 µl of GITC lysis solution (Ambion), 100 µl of 66% or 100% Ethanol or Isopropanol, and 500 ng of lambda genomic DNA. After binding the DNA to the beads, the magnetic particles were separated with a conventional magnet (Magnetic Stand-96, Ambion) and the supernatant removed. The bead pellets were then washed twice with 200 µl of a solution containing 80% ethanol, 100 mM NaCl, 4.5 mM EDTA, and 10 mM Tris (pH 7.5). The dsDNA was eluted in 8 µl of 10 mM Tris (pH 8.0), 1 mM EDTA that was pre-heated to 70° C. and separated on a 1% agarose gel. The DNA was visualized by staining with PicoGreen (Molecular Probes), and fluorescence intensities measured after scanning with a STORM Phosphorimager 860 (Molecular Devices). As shown in FIG. 1, about 25% of the input DNA could be isolated using both ND and ND-SO3H beads.

Example 4

Purification of a dsDNA PCR™ Product using Dextran Particles

Genomic DNA can be isolated using Dextran beads, but the efficiency under the conditions tested was only about 25%. To determine if smaller dsDNA fragments could be recovered with greater efficiency, an 830 bp PCR™ fragment was body labeled with $\alpha^{32}$P-ATP to provide a reporter for binding to and elution from the Dextran magnetic particles. The DNA was purified using DNAclear™ (Ambion). A total of 10 ng of this PCR™ product was then added to 5 µl of 1% ND, ND-SO3H, Charcoal Dextran, or Sicistar-M beads (a magnetic silica bead sold by Micromod, catalog #39-00-153). The DNA was bound in 300 µl containing: i) 2M GITC, 50 mM TrisCl (pH 8.0), 22% isopropanol (G2); ii) 2M GITC, 50 mM TrisCl (pH 8.0), 33% isopropanol (G3); or iii) 1.7M GITC, 43 mM TrisCl (pH 8.0), 44% isopropanol (G4). The sample was incubated for 2-3 min at 23° C., the beads pelleted using the Magnetic Stand-96 (Ambion), and the supernatant removed. The particles were next washed once with the guandinium lysis buffer (200 µl), and twice with a solution containing 80% ethanol (200 µl). Finally, the DNA was eluted in 18 µl of a hot solution (pre-heated to 70° C.) containing 10 mM TrisCl (pH 8.0) and 1 mM EDTA. Samples of the residual beads and the eluate were spotted onto filter paper and the radioactive intensities quantified with a STORM PhosphorImager. As shown in FIG. 2, 50-60% of the input dsDNA could be recovered using the ND and ND-SO3H magnetic beads, whereas a maximum of only ~40% could be recovered with magnetic silica beads. Thus the Dextran beads proved superior to silica particles under these conditions.

Example 5

Double-Stranded DNA can be Efficiently Purified using a Dextran-coated BioMag®Plus Magnetic Particle To assess DNA purification using a different methods for preparing Dextran-coated particles, a custom Dextran bead was prepared by Polysciences, Inc. using their BioMag®Plus magnetic bead platform. The purification of double-stranded DNA was assessed using this particle, and compared with two lots of ND magnetic beads manufactured by Micromod, and an alternative DNA-binding magnetic bead from Agencourt Bioscience Corporation (AMPure®).

Triplicate reactions were performed using 100 ng of input DNA (100 bp ladder, NEB). A total of 100 µg of beads (either ND or BioMag®Plus) were combined with 100 ng DNA (100-1517 bp) in 2.1 M GITC, 0.21% N-lauryl sarcosine, 42 mM sodium citrate, and 42% isopropanol. After binding for 2-3 min, the magnetic particles were separated using a conventional magnet (Magnetic Stand-96, Ambion) and the supernatant removed. The bead pellets were then washed twice with 100 µl of 80% ethanol 10 mM KCl, 2 mM Tris (pH 7.0), 0.2 mM EDTA. Bound dsDNA was eluted in 20 µl nuclease-free water. The eluate was diluted 40-fold in T10E1, and then assayed using Picogreen (Molecular Probes) according to the supplier's protocol. As shown in Table 3, the Dextran BioMag®Plus recovered twice the DNA yield of the ND beads, and slightly more than the AMPure® reagent. Thus, the Dextran BioMag®Plus surface is expected to have utility in any application that requires DNA purification.

TABLE 3

Dextran BioMag ® Plus Particles Recover Twice as Much DNA as Both Nanomag ®-D plain Particles. Values are the average of triplicate reactions.

| Purification Support | % dsDNA Recovery |
| --- | --- |
| ND1 | 43 |
| ND2 | 38 |
| Dextran BioMag ® Plus | 83 |
| AMPure ® | 76 |

Example 6

Total RNA can be Efficiently Purified using a Dextran-coated BioMag®Plus Magnetic Particle Dextran BioMag®Plus magnetic beads were also assessed in RNA purification assays to determine if RNA recovery using these particles was as efficient as the ND beads. Triplicate reactions were performed using 3 µg of total RNA (mouse liver, Ambion). RNA binding was initiated by combining RNA with 100 µg of Dextran-coated particles in 2.1 M GITC, 0.21% N-lauryl sarcosine, 42 mM sodium citrate, and 42% isopropanol. After binding for 2-3 min, the magnetic particles were separated using a conventional magnet (Magnetic Stand-96, Ambion) and the supernatant removed. The bead pellets were then washed twice with 100 µl of 80% ethanol 10 mM KCl, 2 mM Tris (pH 7.0), 0.2 mM EDTA. Bound dsDNA was eluted in 20 µl elution solution (20 µl 1 mM KCl, 0.2 mM sodium citrate (pH 7.0)). The eluate was assayed directly for RNA content by A260 using a NanoDrop spectrophotometer. As shown in Table 4, the Dextran BioMag®Plus recovered as much RNA as the ND beads. Thus, the Dextran BioMag®Plus particles, like the ND particles, are expected to have utility in any application that requires RNA purification.

TABLE 4

Both Nanomag ®-D plain and Dextran BioMag ® Plus Efficiently Purified Total RNA from Solution. Values are the average of triplicate reactions.

| Purification Support | % RNA Recovery |
| --- | --- |
| ND1 | 80 |
| ND2 | 84 |
| Dextran BioMag ® Plus | 83 |

ND1 and ND2 represent two distinct manufacturing lots of the Nanomag Dextran Magnetic Beads.

Example 7

Total RNA can be Efficiently Purified from Fixed Tissue using a Dextran-Coated BioMag®Plus Magnetic Particle with Greater Recovery than Obtainable using a Glass Filter In order to demonstrate the ability of the invention to function with fixed tissue, a mouse liver was dissected from a sacrificed animal, and placed in 10 volumes of 10% neutral buffered formalin on ice for six months at 4° C. A total of 1 µg of the fixed liver tissue was transitioned through the following ethanol (EtOH) treatments: 30% EtOH on ice for 10 min; 40% EtOH on ice for 10 min; 50% EtOH on ice for 10 min; 60% EtOH on ice for 10 min; 70% EtOH on ice for 10 min; 80% EtOH on ice for 10 min; 90% EtOH on ice for 10 min;

and 100% EtOH on ice overnight at 4° C. The tissue was then removed from the EtOH, dried, and placed into 5 mL of Proteinase K Digestion Buffer (3% SDS, 50 mM NaCitrate, 200 mM Tris-HCl at pH 7.5). The sample was homogenized, and 15 mL of Proteinase K Digestion Buffer and 10 mg Proteinase K was added. The lysate was incubated at 50° C. for 4 hours. A total of 50 µl (equivalent to 2.5 mg tissue) was removed to extract the RNA using either a glass fiber filter approach (the mirVana miRNA isolation kit (Ambion Cat#1560)) or a dextran magnetic bead approach (the Mag-MAX total RNA isolation kit (Ambion Cat#1830)).

In a surprising result, the dextran magnetic bead protocol recovered greater than 5-fold more RNA than the glass filter protocol, as quantified by A260 and by quantitative RT-PCR. As a result, the dextran-modified magnetic particles demonstrated an unexpected ability to procure much greater amounts of RNA from fixed tissue than was possible from the conventional method using glass fiber filters.

Example 8

Size Fractionation of dsDNA after Dextran Magnetic Bead Purification

A study was performed to determine the DNA purification efficiency by fragment size. A series of PCR fragments (122, 226, 830, and 1500 bp) were body-labeled with $\alpha^{32}$P-ATP and pooled (2.75-16.7 ng of each size). This pool was then added to 100 µg ND beads in 300 µl of a solution containing 17 mM TrisCl pH 8.0, 33% isopropanol, and either 1.7M GITC or 1.7M NaCl. After binding the DNA to the beads, the magnetic particles were separated with a conventional magnet (Magnetic Stand-96, Ambion) and the supernatant removed. The bead pellets were then washed twice with 200 µl of a solution containing 80% ethanol. The dsDNA was eluted in 20 µl of 10 mM Tris (pH 8.0) that was pre-heated to 70° C. A total of 10 µl of the sample was loaded onto a 5% polyacrylamide gel. The intensities of the recovered radioactive fragments were quantified using a STORM PhosphorImager. As shown in Table 5, dsDNA can be purified with up to 70% efficiency, but there was a reduced recovery of fragments that are 100 nt in length. The "cut-off" for the recovery of DNA less than 100 bp in size is desirable, since it means that unwanted oligodeoxynucleotides are lost during purification.

TABLE 5

Size Fractionation of DNA by Dextran Surfaces.
Percent recovery of each size of dsDNA is given.

|  | 1.5 kb | 830 bp | 226 bp | 100 bp |
|---|---|---|---|---|
| Dextran Beads/GITC | 70.4 | 66.8 | 57.1 | 45.9 |
| Dextran Beads/NaCl | 64.8 | 65.9 | 64.1 | 11.9 |

Example 9

Dextran Surfaces can be used to Remove Contaminating DNA Primers from Solutions

A total of 100 µg of ND plain beads were combined with 100 µg oligodeoxynucleotide comprised of an oligo(dT) and T7 promoter sequence (53 bases in length), and spiked with a trace quantity of the same oligonucleotide that was labelled at the 5' terminus with $^{32}$P. These reagents were mixed in a solution of 17 mM TrisCl pH 8.0, 33% isopropanol, and either 1.7M GITC or 1.7M NaCl. After a 2-3 min incubation at 23° C., the magnetic particles were separated with a conventional magnet (Magnetic Stand-96, Ambion) and the supernatant removed. The bead pellets were then washed twice with 200 µl of a solution containing 80% ethanol. Any DNA that was still bound was eluted in 20 µl of 10 mM Tris (pH 8.0) that was pre-heated to 70° C. As shown in Table 6, less than 4% of the input T7 oligo(dT) primer was recovered, indicating the Dextran beads can effectively purify longer DNA's, such as cDNA's, without carrying over unwanted primers from the cDNA synthesis step. Moreover, this study presents an extreme case, since no DNA fragments >100 bp were present. Such longer DNAs, which would be present in a typical enzymatic reaction that requires purification, would be expected outcompete the poorer binding primers and further reduce the amount of primer carry-over.

TABLE 6

Dextran Magnetic Beads Do Not Recover Small DNA Fragments.

| Salt in Binding Solution | % T7 Oligo(dT) Primer Recovered |
|---|---|
| 1.7 M GITC | 3.0 |
| 1.7 M NaCl | 3.7 |

Example 10

Methods to Enrich and Assay the Dextran Bead Population for the Most Magnetically Responsive Particles Nominal 250 nm ND particles supplied by Micromod typically have a distribution of particle sizes from less than 50 nM to more than 500 nm. During RNA purification (binding in 33% isopropanol and 1.7M NaCl, followed by an 80% ETOH wash and elution in dH20 at 70° C.), these particles deliver >80% RNA yield, but the eluates are tinted with a brownish cast that reflects the loss of some beads from the elution pellet. A stronger color saturation is evident for highly concentrated RNA samples, e.g., when >50 µg of RNA was purified using 100 µg of beads. Bead "drift" from the pellet into the eluates was also particularly pronounced when GITC was used rather than NaCl as the salt in the RNA binding step. Residual beads in the elution will sediment if allowed to incubate for >1 hour on the magnet stand, and can be rapidly removed from solution in a simple centrifugation step. These findings indicate that the most buoyant particles—likely the smallest particles—draw poorly to the magnet. In order to solve this problem, an assay was needed to quantify the amount of color remaining in the elution solution. Serial dilutions of the Dextran beads in a 40 µl volume were made and scanned using UV-Vis scan on a NanoDrop spectrophotometer. The absorbance at 380 nm had a strong linear correlation with bead concentration over a 3 log range (r>0.99) The A380 absorbance data as a function of concentration are given in Table 7. As a result, this spectrophotometric assay can be used to monitor the concentration of residual beads in the eluate.

TABLE 7

An Assay to Measure Residual Dextran Magnetic Beads: Linear Relationship between A380 and Dextran Particle Concentration.

| µg Beads/40 µl | A380 |
|---|---|
| 0.39 | 0.015 |
| 0.78 | 0.035 |
| 3.125 | 0.113 |
| 6.25 | 0.231 |
| 12.5 | 0.461 |
| 25 | 0.912 |
| 50 | 2.062 |
| 100 | 3.19 | r > 0.99

Using this assay, the elution quality (reflected by the A380 signal) of ND bead lots with and without a centrifugation enrichment step were compared (Table 8). Samples were centrifuged at 836×g for 20 min, and the pellet retained. Roughly 60% of the input ND particles were removed in this step. Lots that had been enriched by centrifugation showed a 4-fold improvement in elution quality over magnetically enriched and non-enriched bead lots. It was recognized that the average particle size and polydispersity most influenced elution clarity.

TABLE 8

A Centrifugation Enrichment Step Improves the Clarity of Eluates from Dextran Magnetic Beads and Minimizes Residual Bead Accumulation in the Eluted Samples.

| Cat # | Lot # | Centrifuged? | A380 |
|---|---|---|---|
| 09-00-252 | 1 | No | 0.196 |
| 09-00-252 | 2 | No | 0.201 |
| 09-00-252 | 3 | No | 0.198 |
| 09-00-252 | 4 | Yes | 0.057 |
| 09-00-252 | 5 | Yes | 0.058 |
| 09-00-252 | 6 | Yes | 0.055 |

Example 11

Alternative Salts for Binding Nucleic Acids to Dextran Particles

The inventors hypothesized that a number of salts beside GITC and NaCl would enable the efficient purification of DNA or RNA using ND beads. Consequently, a range of salts and salt concentrations, and alcohol fractions were surveyed to pinpoint alternative binding conditions using an input of 100 ng of DNA (100 bp ladder, NEB cat#N3231S), and standard wash and elution conditions. As shown in Table 9, 0.6M Na2SO3 and 1.7M NaNO3 were substantially as effective as NaCl. Other salts, such as KCl, CsCl, KSCN, KOAc, and NaOAc, allowed the recovery of more than half of the input DNA compared to the best condition of 1.7 M NaCl. In addition, DNA purification was optimal at 33% isopropanol, and 1.66 M NaCl.

would otherwise compromise the intactness of said RNA. Consequently, the following study was performed. Either 25 U wt DNase I (Ambion) or 0.00125 U RNase A (Ambion) was mixed with 1.58 M NaCl, 16.67 mM Tris/33% Isopropanol or 6 M GITC, 16.67 mM Tris/33% Isopropanol. A total of 1 μg of mouse liver total RNA (Ambion) was added, and 50 μg of ND beads provided. After a 2-3 min incubation at 23° C., the magnetic particles were separated with a conventional magnet and the supernatant removed. The bead pellets were then washed twice with 200 μl of a solution containing 80% ethanol. Bound species were eluted in nuclease-free water that was pre-heated to 70° C. The amount of residue nuclease activity was measured by DNaseAlert™ or RNaseAlert™ (Ambion) according to the manufacturer's instructions. A total of 5 μl of the eluate was added to 95 μl 1× DNase I buffer containing DNaseAlert™ substrate or 95 μl 1× RNaseAlert™ buffer containing RNaseAlert™ substrate. Both assays have a limit of detection of <0.5% residual nuclease. Whether GITC or NaCl was used as the binding salt, the removal of DNase I and RNase A during the purification was essentially quantitative (Table 10). Thus, under the conditions described, the Dextran beads selectively purify RNA or DNA without co-purifying significant quantities of proteins such as nucleases.

TABLE 10

Efficiency of Nuclease Removal after Nucleic Acid Purification with Dextran Magnetic Particles.

| Salt in Binding Solution | % DNase I Removed | % RNase A Removed |
|---|---|---|
| GITC | 100 | 99.9 |
| NaCl | 100 | 100 |

Example 13

Purification of RNA from Human Plasma using Dextran Magnetic Beads

For the Dextran beads to have utility for life science applications, it is critical to demonstrate the this surface can isolate RNA from relatively crude biosamples, rather than highly dilute solutions that are free from contaminating protein,

TABLE 9

Salts other than Guandinium and Sodium Chloride can be Used to Purify DNA with Dextran Particles.

| | Normalized % DNA recovery | | Normalized % DNA recovery | Constant IP at 33% | Normalized % DNA recovery | Constant NaCl at 1.7 M | Normalized % DNA recovery |
|---|---|---|---|---|---|---|---|
| LiCl 1.7M | 86 | NH4SO4 0.8M | 8 | NaCl 1.66M | 95 | 33% IP | 100 |
| NaCl 1.7M | 100 | Na2SO4 0.8M | 9 | NaCl 1.33M | 89 | 40% IP | 89 |
| KCl 1.3 M | 67 | Na2SO3 0.6M | 98 | NaCl 1.0 M | 88 | 46.6% IP | 91 |
| CsCl 1.7M | 60 | NaNO3 1.7M | 91 | NaCl 0.66M | 87 | 53.3% IP | 84 |
| NH4Cl 1.7M | 14 | NH4OAc 1.7 M | 34 | NaCl 0.33M | 82 | 60% IP | 81 |
| CaCl2 1.7M | 9 | NaOAc 1M | 52 | NaCl 0M | 67 | 66.6% IP | 75 |
| MgCl2 1.7M | 26 | KOAc 1M | 56 | | | | |
| KSCN 1.7M | 71 | Na-citrate 0.4M | 9 | | | | |

Example 12

Determination of Residual RNase A and DNase I after Purification with Dextran Surfaces An important feature of any RNA purification support is that it can isolate RNA at the exclusion of nucleases that carbohydrates, lipids, etc. Consequently, the following study was performed. A solution containing 67 μl 100% human plasma or 10% human plasma (diluted in water) was combined with 67 μl of a modified guanidinium lysis buffer (6M GITC, 50 mM TrisCl (pH 8.0), and 10 mM EDTA) and 67 μl of 100% isopropanol. After the solutions were mixed, 2 μg of RNA (rat kidney total RNA, Ambion) was added. A total of 5

µl of 5% Dextran beads (either Nanomag Dextran, Nanomag Dextran-SO3H, or Charcoal Dextran) was added, and the sample incubated for 2-3 min at 23° C. The beads were pelleted using the Magnetic Stand-96 (Ambion), and the aqueous solution removed. The Dextran particles were then washed once with the guanidinium lysis buffer, and twice with a solution containing 80% ethanol, 10 mM KCl, 2 mM Tris (pH 7.0), 0.2 mM EDTA. The RNA was eluted in 25 µl of the elution buffer (1 mM Tris (pH 7.0), 5 mM KCl, 0.1 mM EDTA). Table 11 reveals that the input RNA can be efficiently recovered from this "real-world" biosample, even though the background of, e.g., total protein was 100 to 1000 times greater than that of the RNA (assuming ~50 mg/ml of total protein in human plasma). Significantly, silica-based magnetic particles were ineffective in this application as very little RNA could be isolated. Moreover, two very different types of Dextran beads, manufactured by two different companies, proved effective in this application, thus speaking to the general utility of Dextran surfaces in purifying RNA

TABLE 11

Recovery of RNA from Samples Containing Human Plasma.

| Bead Type | % Plasma Challenge | RNA Yield | % Recovery |
|---|---|---|---|
| Nanomag Dextran | 10 | 2.0 µg | 100 |
| Nanomag Dextran-SO3H | 10 | 1.3 µg | 65 |
| Nanomag Dextran-SO3H | 100 | 1.5 µg | 75 |
| Charcoal Dextran | 10 | 1.4 µg | 70 |

Example 14

Functionality of RNA Purified from Dextran Beads in RT-PCR

Figure 3:
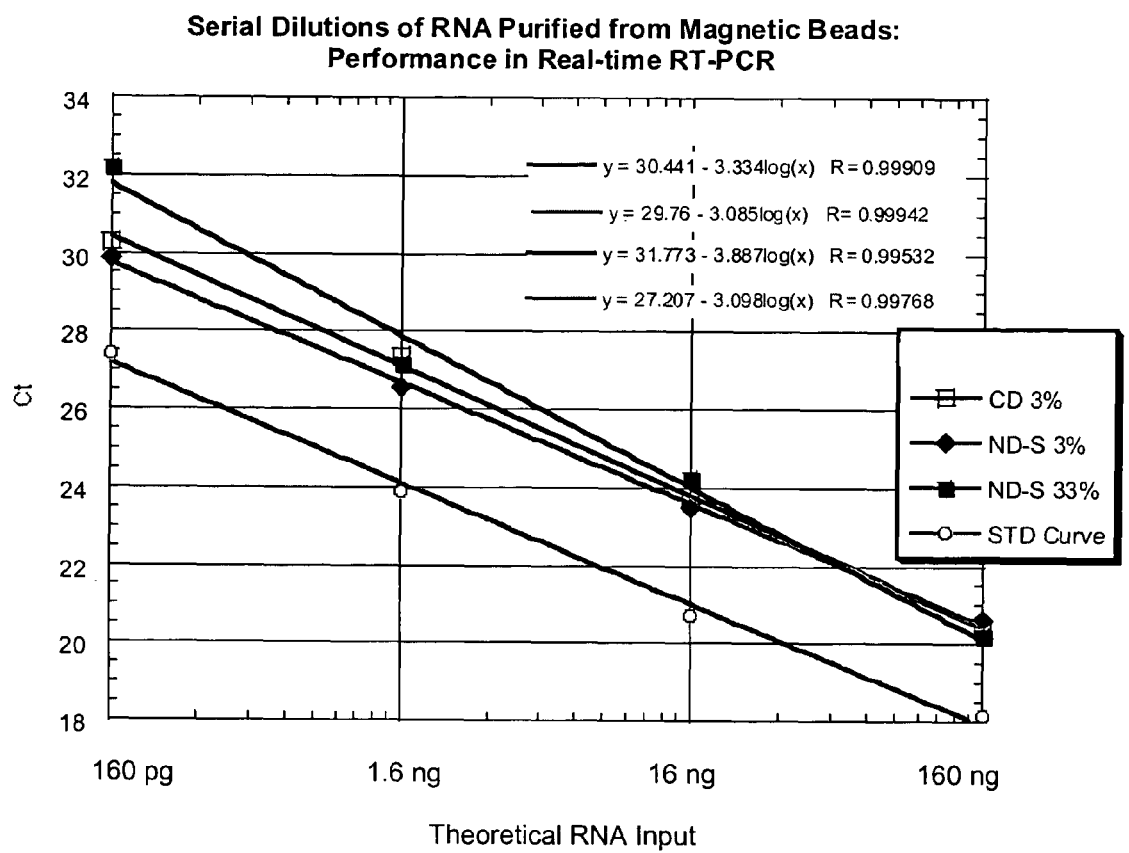
FIG. 3 Real-time RT-PCR standard curves obtained using RNA purified from human plasma with Dextran magnetic particles.

To ensure that the RNA that was eluted from the Dextran beads in Example 13 was competent for RT-PCR, a primer/TaqMan probe set against the rat EGF mRNA was designed. A set of serial dilutions, spanning 2 µl of the eluted RNA to 2 µl of a 1:1000 dilution, were tested in real-time RT-PCR to assess the functionality of the RNA. The RNA was assayed using the MessageSensor RT kit (Ambion) according to the supplier's instructions and using the one-step protocol. For comparison, ten-fold dilutions of the input rat kidney RNA (from 160 ng to 160 pg) were also assayed. All samples were readily detected in RT-PCR, and slopes of the serial dilutions ranged from −3.1 to −3.9 in plots of cycle threshold (Ct) versus theoretical input RNA mass (FIG. 3). These slopes indicate a PCR™ amplification efficiency that is close to ideal. In general, the samples eluted from the Dextran beads were ~2 Ct's lower than the corresponding (stock) RNA control that was not purified. However, the samples characterized in this assay contained 65-75% of the RNA mass present in the control. As a result, the real difference in sensitivity between the control and study samples was ~1.5 Ct, where the variation from sample to sample in real-time RT-PCR is typically at least 0.5 to 1.0 Ct. Moreover, there was no meaningful difference in sensitivity between RNA purified from 10% plasma, and that purified from 100% plasma (the latter being a much "cruder" sample.). Thus these data demonstrate that RNA can be efficiently purified from plasma, and further that this RNA can be readily amplified in RT-PCR to allow quantification of a transcriptional target selected at random from the population of total RNA molecules.

Example 15

Contaminating RNase is not Eluted from Dextran Magnetic Beads

A solution containing 67 µl 100% human plasma was combined with 67 µl of a modified guanidinium lysis buffer (6M GITC, 50 mM TrisCl (pH 8.0), and 10 mM EDTA) and 67 µl of 100% isopropanol. After the solutions were mixed, 2 µg of RNA (rat kidney total RNA, Ambion) was added. A total of 5 µl of 5% Dextran beads (either Nanomag Dextran, Nanomag Dextran-SO3H, or Charcoal Dextran) was added, and the sample incubated for 2-3 min at 23° C. The beads were pelleted using the Magnetic Stand-96 (Ambion), and the aqueous solution removed. The Dextran particles were then washed once with the guanidinium lysis buffer, and twice with a solution containing 80% ethanol, 10 mM KCl, 2 mM Tris (pH 7.0), 0.2 mM EDTA. The RNA was eluted in 25 µl of the elution buffer (1 mM Tris (pH 7.0), 5 mM KCl, 0.1 mM EDTA). One microliter of this eluate was then tested in an extremely sensitive radioisotopic assay design to report RNase activity. This assay employs a radioactive RNA synthesized by in vitro transcription of the RNA substrate. The radioactive RNA was synthesized using a T7 MAXIscript™ transcription kit (Ambion). The in vitro transcription reaction mixture may contain, for example, 1.0 µg of linearized DNA template, 2 µl of 10× transcription buffer, 0.02 µl of UTP[$\alpha$-$^{32}$P] (800 Ci/mmol), 2 µl of each 10 mM ribonucleotide, and 2 µl of the T7 RNA polymerase mix, with a final volume of 20 µl. The reaction is incubated at 37° C. for 30 min. The transcript was purified by phenol:chloroform extraction and used directly for RNase inactivation assay ($2.2 \times 10^5$ counts per minute (approximate specific activity of the probe)/2.3 ng RNA).

A total of 1 µl of the RNA probe was incubated with the test sample in a final volume of 10 µl for 2 hr at 37° C. After incubation, the RNA was fractionated in a denaturing 6 M urea 5% acrylamide gel. The gel was then exposed to x-ray film. Untreated RNA was also fractionated as a control with the test samples for comparative purposes. Test samples containing no detectable RNase activity produced the same single band as the untreated control RNA. RNase activity is indicated by the intensity of the RNA decreasing and by the appearance of smearing below the intact RNA. When one µl of the eluted RNA sample was evaluated in this radioisotopic assay, no significant RNA degradation was observed on the autoradiograph. Since the limit of detection for this assay is only a few femtograms of RNase A, these results demonstrate the beads do not purify any meaningful amounts of RNase A along with the RNA.

Example 16

Dextran and PEG Beads can be Used to Purify RNA from Human Plasma

Figure 4:
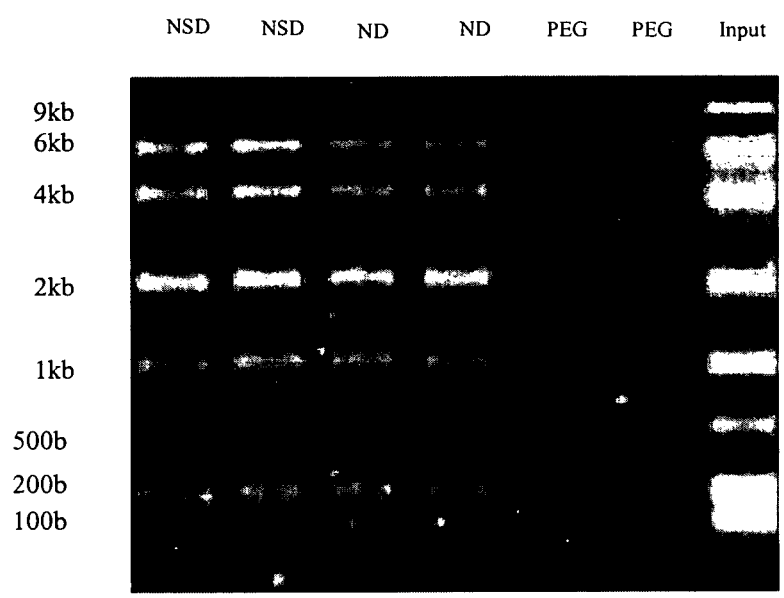
FIG. 4 RNA molecules as small as 100 nucleotides and as large as 9000 nucleotides can be Purified by Dextran- and PEG-coated magnetic particles.

Recovery of different size RNA transcripts from various sample matrices was evaluated using magnetic beads modified with Dextran (ND), Dextran sulfonate (NDS), or PEG. Human plasma (50 µl) was first mixed with 100 µl of the lysis/binding solution (2.5 M GITC, 0.25% N-lauryl sarcosine, 50 mM sodium citrate (pH 7.0), 50% isopropanol) to inactivate nucleases present in the plasma samples. A total of 200 ng of each RNA transcript was then spiked into each sample. Each respective magnetic bead (100 ug) was also added. After a 2-3 min incubation at 23° C., the magnetic particles were separated with a conventional magnet and the supernatant removed. The bead pellets were then successively washed twice with a solution containing 1.7 M GITC, 0.17% N-lauryl sarcosine, 33 mM sodium citrate (pH 7.0), 33% isopropanol, and then twice with 10 mM KCl, 2 mM TrisCl (pH 7.0) and 80% ethanol. The RNA was eluted in 1 mM KCl, 0.2 mM sodium citrate. The eluate was analyzed on a 1% denaturing agarose gel and stained with Ethidium bromide (FIG. 4). The data revealed that RNA as small as 100 b and as large as 9 kb can be purified using either Dextran-, Dextran sulfonate-, or PEG-coated surfaces.

Example 17

Dextran Surfaces Purify RNA from Various Complex Biosample Types

Figure 5:
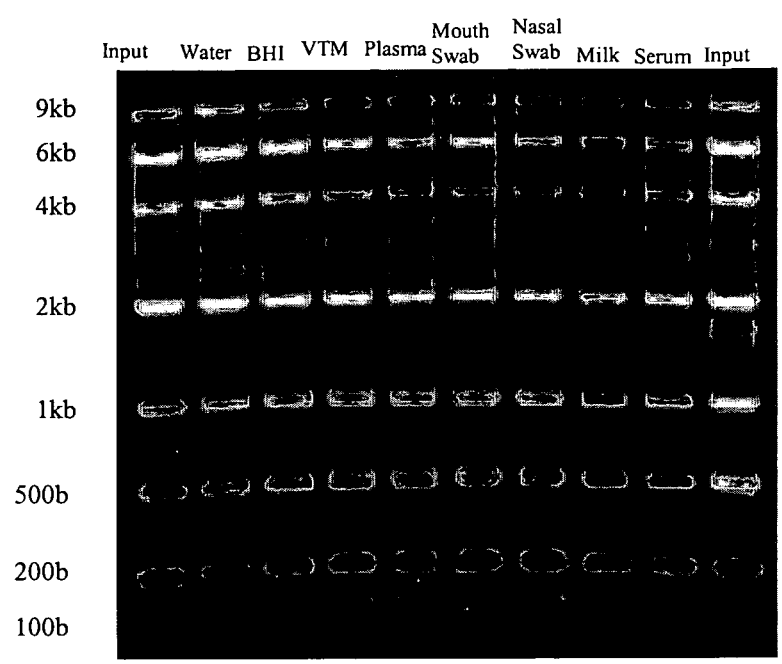
FIG. 5 Dextran magnetic particles recover both large and small RNA molecules from a variety of different sample matrices.

For broad utility, the Dextran magnetic particles should be useful in purifying RNA from a many different sample types. The sample matrix (50 µl of water, brain heart infusion (BHI) media, viral transport media (VTM), mouth and nasal swabs, milk, or serum) was combined with 100 µl of the lysis/binding solution (2.5 M GITC, 0.25% N-lauryl sarcosine, 50 mM sodium citrate (pH 7.0), 50% isopropanol); milk was diluted to 50% with nuclease-free H20. RNA transcripts (250 ng each of 100-9000 nt) were then spiked into all sample media. ND magnetic particles (100 ug) were then added. After a 2-3 min incubation at 23° C., the magnetic particles were separated with a conventional magnet and the supernatant removed. The bead pellets were successively washed twice with a solution containing 1.7 M GITC, 0.17% N-lauryl sarcosine, 33 mM sodium citrate (pH 7.0), 33% isopropanol, and then further washed twice with 10 mM KCl, 2 mM TrisCl (pH 7.0) and 80% ethanol. The RNA was eluted in 1 mM KCl, 0.2 mM sodium citrate (pH 7.0). RNA was analyzed on a 1% denaturing agarose gel and stained with SYBR Gold. FIG. 5 illustrates that high quality intact RNA of various sizes were efficiently and effectively recovered from the different sample matrices.

Example 18

Dextran Particles Purify RNA from Water and Human Plasma Samples to Allow RT-PCR Detection of as Few as 2-3 Transcript Copies An "Alien" control RNA with no known eukaryotic or prokaryotic identity was spiked into a mixture of either water or human plasma in lysis/binding solution (2.5 M GITC, 0.25% N-lauryl sarcosine, 50 mM sodium citrate (pH 7.0), 50% isopropanol) at 20 to 1,000,000 copies. Separately, armored EV (enterovirus) RNA (Ambion) was added to a combination of water or human plasma in lysis/binding solution at the same copy numbers for all samples (50 copies/µL). Carrier RNA (2 µg of poly(A) RNA) was also included to maximize recovery. A total of 100 µg of ND beads were added as the purification support. After a 2-3 min incubation at 23° C., the magnetic particles were separated with a conventional magnet and the supernatant removed. The bead pellets were successively washed twice with a solution containing 1.7 M GITC, 0.17% N-lauryl sarcosine, 33 mM sodium citrate (pH 7.0), 33% isopropanol, and then further washed twice with 10 mM KCl, 2 mM TrisCl (pH 7.0) and 80% ethanol. The RNA was eluted in 1 mM KCl, 0.2 mM sodium citrate (pH 7.0). Carrier RNA recovered was measured by absorbance at 260 nm, and Armored EV RNA and Alien Control RNA were detected by qRT-PCR using 3 µL eluted RNA in 25 µL qRT-PCR reaction. The recovery of carrier RNA was 60-80%. Thus, this protocol enables the highly sensitive detection of RNA transcripts in either water or plasma: as few as 20 copies RNA input could be measured in 400 µL water or plasma (or 2.4 copies input in the actual RT-PCR tube) (Table 12).

TABLE 12

Dextran Particles Purify Low Copy RNA from Water and Human Plasma to Enable High Sensitivity RT-PCR

| | | Alien Control RNA | | | | | | | Armored EV RNA | | Carrier RNA recovered (ug) | |
|---|---|---|---|---|---|---|---|---|---|---|---|---|
| | | Direct in PCR | Water | | | Plasma | | | Water | plasma | | |
| Copy input in Sample | Copy input in RT-PCR | Ct | Ct | Copies | % recvry | Ct | copies | % recvry | Ct | Ct | Water | plasma |
| 1000000 | 120000 | 22.03 | 22.26 | 62570 | 52% | 22.71 | 46190 | 38% | 27.23 | 27.30 | 1.41 | 1.48 |
| | | 22.24 | 22.19 | 65610 | 55% | 22.61 | 49290 | 41% | 27.15 | 27.14 | 1.39 | 1.52 |
| 100000 | 12000 | 25.33 | 25.46 | 7157 | 60% | 26.03 | 4849 | 40% | 27.11 | 27.42 | 1.30 | 1.54 |
| | | 25.38 | 25.42 | 7348 | 61% | 26.14 | 4488 | 37% | 27.03 | 27.34 | 1.41 | ND |
| 10000 | 1200 | 28.68 | 29.05 | 623.6 | 52% | 29.31 | 522.1 | 44% | 27.25 | 27.22 | 1.27 | 1.37 |
| | | 28.81 | 28.9 | 693.1 | 58% | 29.4 | 494 | 41% | 27.16 | 27.44 | 1.46 | 1.39 |
| 1000 | 120 | 32.45 | 32.39 | 64.67 | 54% | 32.57 | 57.46 | 48% | 27.03 | 27.17 | 1.28 | 1.52 |
| | | 32.01 | 32.09 | 79.57 | 66% | 32.57 | 57.44 | 48% | 27.25 | 27.30 | 1.28 | 1.49 |
| 100 | 12 | 35.56 | 35.24 | 9.35 | 78% | 36 | 5.59 | 47% | 27.24 | 27.27 | 1.23 | 1.50 |
| | | 35.50 | 35.97 | 5.71 | 48% | 35.1 | 10.32 | 86% | 27.27 | 27.35 | 1.16 | 1.45 |
| 20 | 2.4 | Not Incl | 38.5 | 1.03 | 43% | No Ct | No Ct | — | 27.36 | 27.31 | 1.58 | 1.57 |
| | | | No Ct | No Ct | — | 37.1 | 2.65 | 110% | 28.12 | 27.36 | 1.37 | 1.49 |

ND, Not Determined

Example 19

Viral RNA Isolation with Dextran Magnetic Particles Offers Superior RT-PCR Sensitivity Compared to Current Best Methods Exotic Newcastle disease virus (END) from clinical tracheal (TR) and cloacal swab (CL) samples was isolated using the Dextran magnetic bead protocol (as given in example 17) or a competitor's protocol, which was a currently NVSL validated filter-based method. Ten-fold less sample volume for each sample was used for the Dextran magnetic bead protocol; the data shown is NOT normalized for sample volume input. As shown in Table 13, more viral RNA was detected from samples using the Dextran magnetic particles as demonstrated by the lower Ct value obtained by qRT-PCR.

TABLE 13

Dextran Magnetic Beads Enable a Viral RNA Isolation Protocol that is More Sensitive than Established Methods.

| Sample ID | Sample type | Dextran Ct | Glass Filter Ct | Normalized Dextran Ct |
|---|---|---|---|---|
| 291939-14 | CL | 36.5 | 37.12 | 33.18 |
| 291939-15 | TR | 34.71 | 34.63 | 31.39 |
| 291939-17 | TR | 33.27 | 33.94 | 29.95 |
| 291939-27 | TR | 27.33 | 27.34 | 24.01 |
| 291939-29 | TR | 27.48 | 26.99 | 24.16 |
| 291937-6 | CL | 38.67 | 35.9 | 35.35 |
| 291937-8 | CL | 37.32 | 37.4 | 34.00 |
| 291937-13 | TR | 28.85 | 33.1 | 25.53 |
| 291937-19 | TR | 33.7 | 32.63 | 30.38 |
| 291935-1 | TR | 34.25 | 36.1 | 30.93 |
| 291935-7 | TR | 34.52 | 36.89 | 31.20 |
| 291935-9 | TR | 35.56 | 37.19 | 32.24 |
| 291935-11 | TR | Neg | 39.87 | — |

Example 20

Utility of Dextran Beads in Total RNA Isolation from Cultured Cells: Linear RNA Recovery with Varying Cell Number Input Three lots of ND beads were used for total RNA isolation from varying cell number inputs of four cell types. The four cell lines used were Hela, K562, A549, and Jurkat; cell number inputs were 500,000, 200,000, 100,000, 1,000 each. "K" in the data summary denotes "1000". 8 units of DNase 1 (2 U/µl) were added to 16 µl of DNase I buffer (preheated at 37° C. for 10 min) and subsequently added to total RNA. Otherwise, the standard protocol was followed (see example 18). Linear RNA recovery was confirmed by qRT-PCR using primers and probe specific for human TATA binding protein (hTBP) (Table 14). No significant difference in RNA recovery was observed among different manufacturing lots of Dextran beads. "RT+" indicates that reverse transcriptase was added to qRT-PCR while "RT−" indicates that no reverse transcriptase was added. Amplification in "RT−" reactions results from residual genomic DNA contamination, and was typically 1000-fold less than-the RNA amount for this transcript target. The data clearly demonstrate that the RNA extracted using Dextran magnetic beads is responsive over a linear range of inputs RT-PCR and is reproducibly quantified.

TABLE 14

RT-PCR Detection of hTBP RT-PCR Reveals Linear RNA Recovery from Various Cultured Cell Lines after Dextran Magnetic Bead Purification.

| Sample | RT+ | | | | RT− | | | |
|---|---|---|---|---|---|---|---|---|
| | Well | Ct | Avg Ct | SD | Well | Ct | Avg Ct | SD |
| HELA_500K_L1 | A1 | 20.2 | 19.95 | 0.412 | I1 | 26.6 | 27.81 | 1.94 |
| | A3 | 20.39 | | | I3 | 29.8 | | |
| | A5 | 19.67 | | | I5 | 29.1 | | |
| | A7 | 19.54 | | | I7 | 25.8 | | |
| HELA_500K_L2 | A9 | 19.61 | 19.54 | 0.091 | I9 | 32.9 | 28 | 3.52 |
| | A11 | 19.6 | | | I11 | 26.7 | | |
| | A13 | 19.56 | | | I13 | 27.7 | | |
| | A15 | 19.41 | | | I15 | 24.7 | | |
| HELA_500K_L3 | A17 | 19.54 | 19.3 | 0.293 | I17 | 25.9 | 25.46 | 0.32 |
| | A19 | 19.34 | | | I19 | 25.4 | | |
| | A21 | 19.45 | | | I21 | 25.4 | | |
| | A23 | 18.88 | | | I23 | 25.1 | | |
| HELA_200K_L1 | B1 | 21.68 | 21.06 | 0.415 | J1 | ND | 33.16 | 3.64 |
| | B3 | 20.9 | | | J3 | 29 | | |
| | B5 | 20.83 | | | J5 | 36 | | |
| | B7 | 20.82 | | | J7 | 34.5 | | |
| HELA_200K_L2 | B9 | 20.7 | 20.79 | 0.133 | J9 | 32.2 | 29.99 | 3 |
| | B11 | 20.76 | | | J11 | 26.8 | | |
| | B13 | 20.99 | | | J13 | 32.9 | | |
| | B15 | 20.73 | | | J15 | 28.2 | | |
| HELA_200K_L3 | B17 | 20.76 | 20.8 | 0.148 | J17 | 31.3 | 31.06 | 3.98 |
| | B19 | 20.62 | | | J19 | 27.9 | | |
| | B21 | 20.85 | | | J21 | 28.4 | | |
| | B23 | 20.97 | | | J23 | 36.6 | | |
| HELA_100K_L1 | C1 | 22.23 | | | K1 | 36 | | |
| | C3 | 21.98 | | | K3 | 35.5 | | |
| | C5 | 21.69 | | | K5 | 30.2 | | |
| | C7 | 21.74 | 21.91 | 0.249 | K7 | 37.4 | 34.78 | 3.13 |
| HELA_100K_L2 | C9 | 21.65 | 21.75 | 0.102 | K9 | 38.5 | 36.16 | 2.03 |
| | C11 | 21.7 | | | K11 | 37.2 | | |
| | C13 | 21.89 | | | K13 | 34.6 | | |
| | C15 | 21.75 | | | K15 | 34.3 | | |
| HELA_100K_L3 | C17 | 21.68 | 21.65 | 0.037 | K17 | 35.2 | 35.56 | 0.37 |
| | C19 | 21.66 | | | K19 | 35.3 | | |
| | C21 | 21.59 | | | K21 | 36 | | |
| | C23 | 21.66 | | | K23 | 35.8 | | |
| HELA_1K_L1 | D1 | 29.16 | 29.19 | 0.136 | L1 | ND | 36.35 | |
| | D3 | 29.2 | | | L3 | ND | | |
| | D5 | 29.03 | | | L5 | ND | | |
| | D7 | 29.36 | | | L7 | 36.4 | | |

TABLE 14-continued

RT-PCR Detection of hTBP RT-PCR Reveals Linear RNA Recovery from Various Cultured Cell Lines after Dextran Magnetic Bead Purification.

| Sample | RT+ | | | | RT- | | | |
|---|---|---|---|---|---|---|---|---|
| | Well | Ct | Avg Ct | SD | Well | Ct | Avg Ct | SD |
| HELA_1K_L2 | D9 | 29.27 | 29.28 | 0.119 | L9 | ND | ND | |
| | D11 | 29.15 | | | L11 | ND | | |
| | D13 | 29.27 | | | L13 | ND | | |
| | D15 | 29.44 | | | L15 | ND | | |
| HELA_1K_L3 | D17 | 29.29 | 29.06 | 0.208 | L17 | ND | 37.28 | ND |
| | D19 | 28.91 | | | L19 | ND | | |
| | D21 | 29.17 | | | L21 | 37.3 | | |
| | D23 | 28.85 | | | L23 | ND | | |
| A549_500K_L1 | E1 | 20.68 | 20.43 | 0.199 | M1 | 28 | 25.73 | 1.55 |
| | E3 | 20.37 | | | M3 | 24.9 | | |
| | E5 | 20.2 | | | M5 | 25.3 | | |
| | E7 | 20.46 | | | M7 | 24.7 | | |
| A549_200K_L1 | F1 | 21.75 | 21.53 | 0.144 | N1 | 36 | 32.95 | 3.02 |
| | F3 | 21.46 | | | N3 | 28.8 | | |
| | F5 | 21.45 | | | N5 | 33.3 | | |
| | F7 | 21.47 | | | N7 | 33.8 | | |
| A549_100K_L1 | G1 | 22.72 | | | O1 | 37.9 | | |
| | G3 | 22.58 | | | O3 | ND | | |
| | G5 | 22.48 | 22.6 | 0.098 | O5 | 37.7 | 37.8 | 0.16 |
| | G7 | 22.62 | | | O7 | ND | | |
| A549_1K_L1 | H1 | 30 | 30.11 | 0.077 | P1 | ND | ND | ND |
| | H3 | 30.13 | | | P3 | ND | | |
| | H5 | 30.14 | | | P5 | ND | | |
| | H7 | 30.18 | | | P7 | ND | | |
| K562_500K_L1 | A2 | 18.29 | 18.14 | 0.124 | I2 | 23.5 | 24.45 | 0.81 |
| | A4 | 18.12 | | | I4 | 25.4 | | |
| | A6 | 17.99 | | | I6 | 24.1 | | |
| | A8 | 18.16 | | | I8 | 24.7 | | |
| K562_500K_L2 | A10 | 18.1 | 17.88 | 0.173 | I10 | 32.4 | 26.82 | 3.75 |
| | A12 | 17.68 | | | I12 | 25.3 | | |
| | A14 | 17.9 | | | I14 | 24.5 | | |
| | A16 | 17.85 | | | I16 | 25 | | |
| K562_500K_L3 | A18 | 17.95 | 17.94 | 0.069 | I18 | 23.3 | 23.65 | 0.34 |
| | A20 | 17.9 | | | I20 | 23.5 | | |
| | A22 | 17.87 | | | I22 | 23.9 | | |
| | A24 | 18.03 | | | I24 | 24 | | |
| K562_200K_L1 | B2 | 19.01 | 19.4 | 0.274 | J2 | 26.5 | 28.58 | 2.73 |
| | B4 | 19.65 | | | J4 | 28.6 | | |
| | B6 | 19.51 | | | J6 | 26.8 | | |
| | B8 | 19.41 | | | J8 | 32.4 | | |
| K562_200K_L2 | B10 | 19.33 | 19.27 | 0.044 | J10 | 28.1 | 27.87 | 0.7 |
| | B12 | 19.27 | | | J12 | 28.7 | | |
| | B14 | 19.28 | | | J14 | 27.6 | | |
| | B16 | 19.22 | | | J16 | 27.1 | | |
| K562_200K_L3 | B18 | 19.33 | 19.26 | 0.064 | J18 | 27 | 27.11 | 0.34 |
| | B20 | 19.29 | | | J20 | 26.7 | | |
| | B22 | 19.18 | | | J22 | 27.5 | | |
| | B24 | 19.25 | | | J24 | 27.2 | | |
| K562_100K_L1 | C2 | 20.32 | | | K2 | 32.9 | | |
| | C4 | 20.54 | 20.34 | 0.137 | K4 | 32.7 | 33.01 | 0.32 |
| | C6 | 20.28 | | | K6 | 33 | | |
| | C8 | 20.23 | | | K8 | 33.4 | | |
| K562_100K_L2 | C10 | 20.12 | 20.15 | 0.045 | K10 | 34 | 33.04 | 1.02 |
| | C12 | 20.13 | | | K12 | 33.7 | | |
| | C14 | 20.12 | | | K14 | 31.8 | | |
| | C16 | 20.22 | | | K16 | 32.7 | | |
| K562_100K_L3 | C18 | 20.18 | 20.13 | 0.082 | K18 | 32.9 | 32.52 | 0.52 |
| | C20 | 20.18 | | | K20 | 31.7 | | |
| | C22 | 20.01 | | | K22 | 32.7 | | |
| | C24 | 20.14 | | | K24 | 32.7 | | |
| K562_1K_L1 | D2 | 27.85 | 27.61 | 0.246 | L2 | ND | 35.66 | |
| | D4 | 27.73 | | | L4 | ND | | |
| | D6 | 27.6 | | | L6 | ND | | |
| | D8 | 27.28 | | | L8 | 35.7 | | |
| K562_1K_L2 | D10 | 27.21 | 27.33 | 0.106 | L10 | 36.2 | 36.19 | |
| | D12 | 27.28 | | | L12 | ND | | |
| | D14 | 27.42 | | | L14 | ND | | |
| | D16 | 27.43 | | | L16 | ND | | |
| K562_1K_L3 | D18 | 27.39 | 27.34 | 0.135 | L18 | ND | 36.58 | |
| | D20 | 27.42 | | | L20 | 36.6 | | |
| | D22 | 27.4 | | | L22 | ND | | |
| | D24 | 27.14 | | | L24 | ND | | |

TABLE 14-continued

RT-PCR Detection of hTBP RT-PCR Reveals Linear RNA Recovery from Various Cultured Cell Lines after Dextran Magnetic Bead Purification.

| Sample | RT+ | | | | RT- | | | |
|---|---|---|---|---|---|---|---|---|
| | Well | Ct | Avg Ct | SD | Well | Ct | Avg Ct | SD |
| Jrkat_500K_L1 | E2 | 20.07 | 20.07 | 0.087 | M2 | 25.3 | 26.42 | 1.05 |
| | E4 | 19.96 | | | M4 | 26 | | |
| | E6 | 20.11 | | | M6 | 26.6 | | |
| | E8 | 20.16 | | | M8 | 27.8 | | |
| Jrkat_200K_L1 | F2 | 21.54 | 21.51 | 0.098 | N2 | 33.1 | 35.25 | 2.17 |
| | F4 | 21.63 | | | N4 | 37.4 | | |
| | F6 | 21.4 | | | N6 | 36.8 | | |
| | F8 | 21.48 | | | N8 | 33.7 | | |
| Jrkat_100K_L1 | G2 | 23 | 22.67 | 0.229 | O2 | 35 | 35.98 | 1.33 |
| | G4 | 22.64 | | | O4 | 37.9 | | |
| | G6 | 22.48 | | | O6 | 35.5 | | |
| | G8 | 22.56 | | | O8 | 35.5 | | |
| Jrkat_1K_L1 | H2 | 31.81 | 31.59 | 0.415 | P2 | ND | 37.32 | 1.73 |
| | H4 | 31.23 | | | P4 | 39.1 | | |
| | H6 | 31.24 | | | P6 | 37.2 | | |
| | H8 | 32.06 | | | P8 | 35.6 | | |

Example 21

Purification of RNA from Biological Tissue using Dextran Magnetic Beads

Figure 6:
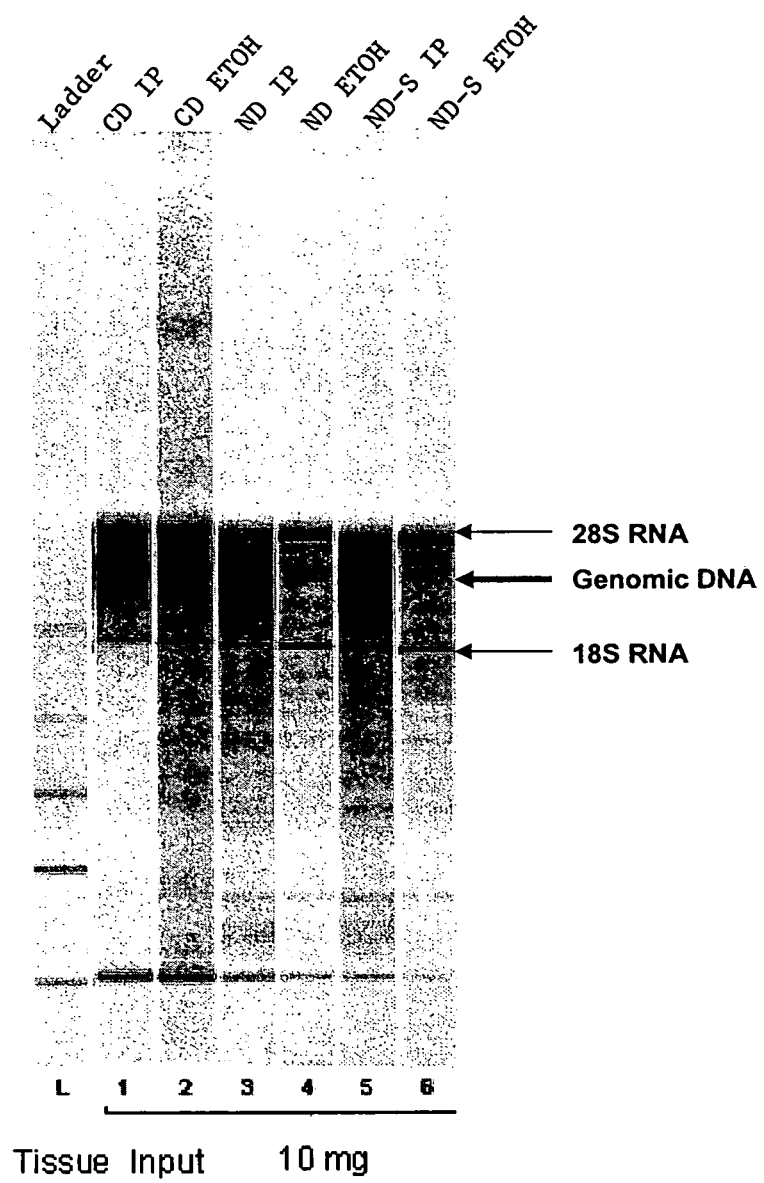
FIG. 6 Electrophoretic profile of RNA purified from frozen mouse spleen tissue using Dextran magnetic particles and various binding buffers.

To determine if the Dextran beads can purify total RNA from tissues, the following study was performed. Three mouse spleens (flash frozen, Pel-Freez) were homogenized in GITC lysis buffer (RNAqueous kit, Ambion) to a create a lysate (108 mg/ml). Endogenous RNA from this lysate was bound to the magnetic particles by combining 100 µl lysate (10.8 mg tissue equivalent) with 200 µl of 0.5× GITC lysis solution in 33% ETOH or 33% isopropanol and 5 µl of a 5% solution of Dextran beads. The sample was incubated for 2-3 min at 23° C. The beads were then pelleted using the Magnetic Stand-96 (Ambion), and the aqueous solution removed. The Dextran particles were next washed once with the guanidinium lysis buffer (200 µl), and twice with a solution containing 80% ethanol (200 µl). The RNA was eluted in 30 µl of a solution containing 10 mM TrisCl (pH 8.0) and 1 mM EDTA. As shown in Table 15, the Nanomag Dextran and Nanomag Dextran SO3H beads allowed RNA from the spleen tissue to be recovered in high yield. Charcoal Dextran, by comparison, recovered only 10-15% of the RNA isolated using the Nanomag beads. Importantly, the RNA purified by each of the Dextran beads was highly intact (FIG. 6). In addition, the electrophoretic profile of the RNA isolated with Dextran microparticles reveals that genomic DNA can be recovered if 33% isopropanol is used, but said DNA is substantially absent is 33% ethanol is used. Thus the nature of the organic component in the binding solution can modulate the recovery of RNA at the exclusion of DNA, or the recovery of total nucleic acid when Dextran beads are used as the purification support.

TABLE 15

RNA Yields from Mouse Spleen Tissue using Dextran Beads.

| Bead | Solvent | RNA Yield (ug) |
|---|---|---|
| Charcoal Dextran | Isopropanol | 1.8 |
| ND | Isopropanol | 10.4 |
| ND-SO3H | Isopropanol | 15.7 |

TABLE 15-continued

RNA Yields from Mouse Spleen Tissue using Dextran Beads.

| Bead | Solvent | RNA Yield (ug) |
|---|---|---|
| Charcoal Dextran | Ethanol | 1.5 |
| ND | Ethanol | 12.7 |
| ND-SO3H | Ethanol | 17.0 |

Example 22

Purification of a RNA by PEG-coated Magnetic Particles

Magnetic particles (250 nm) coated with PEG 300 are available from Micromod (Germany). RNA purification using these particles was evaluated in the following experiment: 32 µg of unmodified RNA amplified with MessageAmp II (Ambion) was combined with 50 µg of Nanomag PEG or ND particles. Binding conditions included either 1.7M NaCl, 1.7 M GITC, or 1.45 M NaCl/Urea in the presence of 33% ispropanol. All purification reactions were performed in an 96 well polystyrene plate. The components were added, mixed, and incubated for 10 min at RT. The plate was then placed on a 96 well magnetic plate stand for 15 min to allow the beads to pellet. The supernatant was removed, the samples were washed twice with 80% ethanol, and RNA was eluted in dH2O at 70° C. Concentration of the purified aRNA samples was measured on a NanoDrop spectrophotometer. As shown in the Table 16, Nanomag PEG beads recovered as much RNA as ND beads in all conditions. This finding demonstrates the utility of PEG coated magnetic particles for RNA purification.

TABLE 16

PEG Magnetic Beads Efficiently Purify Amplified RNA.

| Binding Condition | Surface Chemistry | avg % Yield |
|---|---|---|
| 1.7M NaCl | Nanomag-PEG | 106 |
| 1.7M GITC | Nanomag-PEG | 102 |
| 1.45 Mea NaCl/Urea | Nanomag-PEG | 104 |

TABLE 16-continued

PEG Magnetic Beads Efficiently Purify Amplified RNA.

| Binding Condition | Surface Chemistry | avg % Yield |
|---|---|---|
| 1.7M NaCl | Nanomag-Dextran | 100 |
| 1.7M GITC | Nanomag-Dextran | 97 |
| 1.45 Mea NaCl/Urea | Nanomag-Dextran | 99 |

Example 23

Dextran Beads Efficiently Purify cDNA to Allow High Yields of Amplified RNA

A total of 1 µg HeLa-S3 total RNA (Ambion cat# 7852) was amplified in duplicate reactions using Ambion's MessageAmp II kit, according to the manufacturer's instructions. In an additional duplicate set of reactions, the manufacturer's protocol was observed with the exception that the cDNA purification step with glass filter columns was replaced by magnetic bead purification using ND particles. The cDNA (100 µl) was bound to 100 µg of ND beads in 17 mM TrisCl pH 8.0, 33% isopropanol, and 1.7M NaCl. After a 2-3 min incubation at 23° C., the magnetic particles were separated with a conventional magnet (Magnetic Stand-96, Ambion) and the supernatant removed. The bead pellets were then washed twice with 200 µl of a solution containing 80% ethanol, and the bound cDNA eluted in 20 µl of nuclease-free water. In vitro transcription was performed for 4 hours for all reactions. As shown in Table 17, the substitution of ND beads for a glass filter purification step at the level of cDNA cleanup resulting in 80 µg of aRNA, compared to 90 µg aRNA for the control. The average length resulting aRNA was actually slightly longer, ~1308 nt vs. ~1238 nt. Thus, the ND beads are very effective in purifying cDNA to allow efficient RNA amplification, and 2660-fold amplification could be accomplished in a single round (assuming 3% of total RNA as mRNA). Moreover, there was no selective loss in subpopulations of DNA lengths that might otherwise undermine the goal of global representation of the amplified RNA.

TABLE 17

Dextran Surfaces Can be Used to Purify cDNA During RNA Amplification.

| cDNA Purification Method | aRNA yield | Avg aRNA yield | Avg length of aRNA | % aRNA yield compared to glass filter | Approximate Fold Amplification of input RNA |
|---|---|---|---|---|---|
| ND | 82 | | 1315 | | |
| ND | 78 | 79.8 | 1300 | 89 | 2660 |
| Glass Filter | 95 | | 1225 | | |
| Glass Filter | 85 | 90.0 | 1250 | 100 | 3000 |

Example 24

Dextran Beads Purify Nucleic Acid without Unwanted Contamination by Nucleotides or Cyanine Dyes A total of 100 µg of ND plain beads were combined with 7.5 mM of ATP, GTP, CTP, TTP, or 1.88 mM Biotin-UTP, or 3.75 mM amino allyl-UTP, or 80% of a single pack of Cy5 dye (CyScribe™ Cy6 reactive dye, Amersham) in Ambion's MEGAscript transcription buffer. These reagents were mixed in a solution of 17 mM TrisCl pH 8.0, 33% isopropanol, and 1.6 M NaCl. After a 2-3 min incubation at 23° C., the magnetic particles were separated with a conventional magnet (Magnetic Stand-96, Ambion) and the supernatant removed. The bead pellets were then washed twice with 200 µl of a solution containing 80% ethanol: Any nucleotides that were still bound were eluted in 20 µl of nuclease-free water that was pre-heated to 70° C. The percentage of residual nucleotide was measured by quantification of the A260 absorbance using a NanoDrop spectrophotometer, and the appropriate extinction coefficients for each nucleotide species. As shown in Table 18, less than 4% of any nucleotide was recovered, indicating that the Dextran beads have little affinity for nucleotides, and this species can be efficiently separated from >100 b RNA during purification. This finding is significant as it applies to the purification of aRNA, where residual modified nucleotides can elevate the background signal from a microarray. Moreover, this study presents an extreme case, since no RNA fragments >100 b were present. These longer RNAs, which would be present in a typical enzymatic reaction that requires purification, would be expected outcompete the poorer binding primers and further reduce the amount of primer carry-over.

TABLE 18

Unmodified and Modified Nucleotides and Cy5 Fluorescent Dye are not Recovered after Nucleic Acid Purification with Dextran Magnetic Beads.

| Nucleotide Added | % Recovery of Input Nucleotide |
|---|---|
| ATP, GTP, CTP, TTP | 1.5% |
| Biotin-UTP | 0.8% |
| Amino allyl UTP | 3.6% |
| Cy5 dye | ND |

ND, Not Detectable

Example 25

PEG-Coated Surfaces Enable RNA Purification without Contaminating Nucleotides

A total of 100 µg of PEG magnetic beads were combined with 7.5 mM (each) of ATP, GTP, CTP, TTP, or 1.88 mM Biotin-UTP (Enzo), or 3.75 mM amino allyl-UTP (Ambion), or 80% of a single pack of Cy5 dye (Cyscribe Cy5 reactive dye, Amersham) in Ambion's MEGAscript transcription buffer. These reagents were mixed in a solution of 17 mM TrisCl pH 8.0, 33% isopropanol, and 1.6M NaCl . After a 2-3 min incubation at 23° C., the magnetic particles were separated with a conventional magnet (Magnetic Stand-96, Ambion) and the supernatant removed. The bead pellets were then washed twice with 200 μl of a solution containing 80% ethanol. Any nucleotides that were still bound were eluted in 40 μl of nuclease-free water that was pre-heated to 70° C. The percentage of residual nucleotide was measured by quantification of the A260 absorbance using a NanoDrop spectrophotometer, and the appropriate extinction coefficients for each nucleotide species. As shown in Table 19, less than 3% of any nucleotide was recovered, indicating that the PEG beads have little affinity for nucleotides, and this species can be efficiently separated from >100 b RNA during purification. This finding is significant as it applies to the purification of aRNA, where residual modified nucleotides can elevate the background signal from a microarray. Moreover, this study presents an extreme case, since no RNA fragments >100 b were present. These longer RNAs, which would be present in a typical enzymatic reaction that requires purification, would be expected outcompete the poorer binding primers and further reduce the amount of primer carry-over.

TABLE 19

Unmodified and Modified Nucleotides are not Recovered after Nucleic Acid Purification with PEG Magnetic Beads.

| Nucleotide Added | % Recovery of Input Nucleotide |
|---|---|
| ATP, GTP, CTP, TTP | 1.3 |
| Biotin-UTP | 0.7 |
| Amino allyl UTP | 2.2 | in 17 mM TrisCl pH 8.0, 33% isopropanol, and 1.7M NaCl. After a 2-3 min incubation at 23° C., the magnetic particles were separated with a conventional magnet and the supernatant removed. The bead pellets were then washed twice with 200 μl of a solution containing 80% ethanol, and the bound cDNA eluted in 20 μl of nuclease-free water.

The aRNA (40 μl) was diluted to 100 μl with nuclease-free water, and processed in the same manner as described for cDNA purification with ND beads. The nucleotide pool for all in vitro transcription reactions (4 hr incubation) was doped with either biotin-UTP/biotin-CTP or amino allyl-UTP to mimic a typical RNA amplification reaction that is destined for microarray analysis.

As shown in Table 20, the substitution of ND beads for a glass filter purification step at the level of both cDNA and aRNA clean-up resulted in 74-79% of the aRNA yield of the glass filter samples. The average length resulting labeled aRNA was approximately the same or slightly longer. Thus, the ND beads are very effective in purifying cDNA and labeled aRNA in the context of a complete RNA amplification reaction. Moreover, there was no selective loss in subpopulations of DNA lengths that might otherwise undermine the goal of global representation of the amplified RNA.

TABLE 20

Dextran Surfaces Purify Both cDNA and Modified aRNA During RNA Amplification.

| cDNA Purification Method | aRNA Purification Method | Yield (ug) | Avg Yield (ug) | Avg length of aRNA | % aRNA yield compared to glass fliter |
|---|---|---|---|---|---|
| Filter Biotin-1 | Filter | 37.4 | | 1370 | |
| Filter Biotin-2 | Filter | 39.3 | 38.4 | 1350 | 100 |
| Filter amino allyl-1 | Filter | _19.3_ | | 955 | |
| Filter amino allyl-2 | Filter | 32.2 | 32.2 | 1000 | 100 |
| ND Biotin-1 | ND | 28.9 | | _830_ | |
| ND Biotin-2 | ND | 27.8 | 28.4 | 1330 | 74 |
| ND amino allyl-1 | ND | 23.1 | | 1110 | |
| ND amino allyl-2 | ND | 27.8 | 25.4 | 1075 | 79 |

Underlined values are outlier data.

Example 26

Dextran Beads Efficiently Purify cDNA and Labelled Amplified RNA in an RNA Amplification Procedure A total of 500 ng HeLa—S3 total RNA (Ambion) was amplified in duplicate reactions using Ambion's MessageAmp II kit, according to the manufacturer's instructions. In an additional duplicate set of reactions, the manufacturer's protocol was altered by using ND magnetic beads, instead of glass filter columns, to purify both cDNA (after second strand cDNA synthesis step) and aRNA (after in vitro transcription step). The cDNA (100 μl) was bound to 100 μg of ND beads Example 27

Dextran Particles are Compatible with Streamlined Procedures for in Vitro Transcription Since the same Dextran beads can be used to purify both cDNA and aRNA in an RNA amplification procedure, the inventors reasoned that the procedure could be streamlined if the beads were simply left in solution after cDNA purification. The benefit of this strategy is that the beads, present in solution during in vitro transcription (IVT), would be available for aRNA purification immediately after the transcription step, and a separate addition of beads would be unnecessary. This economical approach would minimize handling of the sample, and potential reduce error and increase reproducibility.

Consequently, 100 µg of ND beads were added to a MEGAscript transcription reaction (Ambion), performed according to the supplier's instructions using 100 ng pTRI-Xefl plasmid template. A control reaction that did not contain any beads was included for comparison. After a 4 hour reaction, RNA (100 µl) was bound to 100 µg of ND beads (added to the control reaction, or already present in the study sample) in 17 mM TrisCl pH 8.0, 33% isopropanol, and 1.7M NaCl. After a 2-3 min incubation at 23° C., the magnetic particles were separated with a conventional magnet and the supernatant removed. The bead pellets were then washed twice with 200 µl of a solution containing 80% ethanol, and the bound cDNA eluted in 40 µl of nuclease-free water. A total of 1 µl of the eluate was separated on an RNA LabChip, and the RNA yield computed after analysis using Agilent 2100 Bioanalyzer software. Table 21 reveals that the RNA yield was largely unaffected by the presence of Dextran beads during the IVT step. As a result, the reaction can be notably streamlined by this approach.

TABLE 21

The Presence of 100 µg of Dextran Particles During in vitro Transcription Does Not Significantly Reduce the Yield of Synthesized RNA

| Sample | RNA yield (ug) |
|---|---|
| IVT | 2.4 |
| IVT + 100 µg ND Beads | 2.1 |

Example 28

Dextran Particles Efficiently Purify RNA Composed of Modified Nucleosides

RNA molecules containing modified nucleosides are used as reporters in microarray protocols. The ability of ND beads (250 nm) to purify amino allyl, Cy or biotin modified RNAs were evaluated, and compared to the RNA clean™ product, an RNA-binding magnetic particle from Agencourt Bioscience Corp. Since the in vitro transcription reactions typically produce high yields of these modified RNAs, each purification reaction was challenged with high input amounts of modified aRNA. Cy labelled Xef transcripts were made using Ambion's MegaScript kit with Cy modified nucleotides. Cy labelled RNA amplified from Hela total RNA was made using Ambion's MessageAmp kit with Cy modified nucleotides. Using optimized binding conditions, the purification as much as 20 µg Cy modified Xef aRNA and as much as 10 µg Cy modified Hela total aRNA was assayed per reaction. Purification reactions were perfomed in a 96 well plate with the following components: 100 µg ND particles, 1.7M NaCl, 17 mM Tris pH 8, and 33% isopropanol. In addition, 0.33X IVT buffer and T7RNA polymerase (800 U/rxn) were added to mimic carryover from IVT. For each reaction, the above components were mixed well and allowed to incubate at RT for 10 min before being placed on a 96 well magnetic stand (Ambion) for 20 min to pellet the particles. The binding supernatant was removed and the beads washed twice with 80% ethanol followed by elution in dH2O at 70° C. Results were measured using a NanoDrop spectrophotometer. ND particles yielded as much as 93% of the input Cy modified Xef RNA (Table 22). A similar trend held for purification of Cy modified aRNA amplified from Hela total RNA, which yielded a recovery of 81%. These results demonstrate that Dextran particles are effective for binding RNAs modified with bulky and hydrophobic Cy modifications. Furthermore, Dextran magnetic beads recovered 50% more Cy-modified RNA than the RNAclean™ magnetic particle.

Biotinylated and amino allyl modified aRNAs were made using appropriate modified nucleotides in MessageAmp RNA amplification reactions. To achieve uniform RNA input over many reactions, separate stocks were made from pools of biotinylated and amino allyl modified RNA samples. Binding reactions were performed using the conditions cited above, but the reaction was scaled down two-fold (50 µg beads to bind 75 µg of modified RNA) due to volume constraints in the 96 well plates. ND particles yielded >80% of both modified aRNAs (Table 22). These data indicate that Dextran coated particles can be used to purify and "clean up" modified RNAs from in vitro transcription reactions.

TABLE 22

Dextran Surfaces Purify Modified aRNAs More Efficiently Than Other Commercially Available RNA-binding Magnetic Beads

| RNA | Input | Bead | Yield (%) |
|---|---|---|---|
| Cy modified Xef transcript | 20 µg | ND | 93 |
| Cy modified Xef transcript | 20 µg | RNAclean ™ | 60 |
| Cy Modified Hela aRNA | 10 µg | ND | 81 |
| Cy Modified Hela aRNA | 10 µg | RNAclean ™ | 55 |
| Unmodified aRNA | 100 µg | ND | 86 |
| Unmodified aRNA | 100 µg | RNAclean ™ | 78 |
| Unmodified aRNA | 150 µg | ND | 77 |
| Unmodified aRNA | 150 µg | RNAclean ™ | 66 |
| Amino Allyl Modified aRNA | 75 µg | ND | 83 |
| Amino Allyl Modified aRNA | 75 µg | RNAclean ™ | 86 |
| Biotinylated aRNA | 75 µg | ND | 82 |
| Biotinylated aRNA | 75 µg | RNAclean ™ | 75 |

Example 29

Dextran Magnetic Beads Efficiently Purify Amplified Biotinylated or Amino Allyl RNA and Enable Microarray Concordance with Standard RNA Amplification Methods A study was performed to compare aRNA purification using Dextran beads with the more conventional glass fiber-based method. HeLa total RNA (Ambion) was used at an input at 0.1 µg or 1 µg per RNA amplification reaction. Ambion's MessageAmp II reagents and protocols were used for the first strand cDNA and second strand cDNA synthesis, as well as for the in vitro transcription reaction to synthesize amplified RNA. Two distinct reaction times, 4 and 14 hr, were employed for the in vitro transcription step. The Dextran bead method for amplified RNA purification, combined with a carboxylate bead-based method (AMPure®, Agencourt Bioscience Corp.) for double-strand cDNA cleanup, was compared to standard MessageAmp protocol which uses glass fiber spin columns for both double-stranded cDNA and aRNA purification.

Purification of amplified RNA was accomplished through the following protocol. The in vitro transcription reaction (40 µl) was combined with 100 µl of aRNA binding solution (5M GITC, 0.5% N-lauryl sarcosine, 100 mM sodium acetate (pH 7.0) and 20 µl of a suspension containing ND beads (100 µg of particles in 1M GITC, 0.1% N-lauryl sarcosine, 20 mM sodium citrate (pH 7.0), and 30% isopropanol). The solution was agitated in the bottom of a U-bottom 96-well plate for 2 min, and set on a magnetic stand for 3-5 min. The supernatant was removed the beads were washed twice with 80% ethanol, 10 mM KCl, 2 mM Tris (pH 7.0), and 0.2 mM EDTA. After the second wash, the aRNA was eluted in 40 μl of 1 mM KCl, 0.2 mM sodium citrate (pH 7.0).

Three replicates were performed for each condition tested. For all conditions, the dextran particle protocol resulted in better yield and at least equivalent quality (i.e., RNA size distribution) of amplified RNA as the standard glass fiber spin column protocol (Table 23). When applied to Affymetrix's GeneChip human focus array, the two methods resulted in the same background, signal intensity, percentage of present calls with a very high correlation (>99.5%) (Tables 24 and 25).

TABLE 23

A Dextran Magnetic Bead-based Plate Platform Generates Higher aRNA Yields Than a Glass Filter Platform. Plate = Dextran magnetic bead platform; Tube = Glass filter spin column.

| IVT time | μg input | Method | Biotin aRNA yield (ug) | Standard Dev in aRNA yield ug | Standard Dev in aRNA yield % | Mean aRNA Size (nt) |
|---|---|---|---|---|---|---|
| 4 hr | 0.1 | Tube | 4.98 | 0.42 | 9% | 1300 |
|  |  | Plate | 12.67 | 1.77 | 14% | 1200 |
|  | 1 | Tube | 64.02 | 8.88 | 14% | 1800 |
|  |  | Plate | 70.18 | 12.89 | 18% | 1800 |
| 14 hr | 0.1 | Tube | 19.54 | 1.99 | 10% | 1100 |
|  |  | Plate | 26.82 | 2.33 | 9% | 1200 |
|  | 1 | Tube | 139.62 | 8.69 | 6% | 2000 |
|  |  | Plate | 147.61 | 17.9 | 12% | 2000 |

TABLE 24

Microarray Performance: Dextran Bead Plate Platform Compared to Glass Filter Purification in Single Tubes.

| RNA Input | IVT time | Protocol | 3'/5' ratio GAPDH | 3'/5' ratio β-actin | Present calls |
|---|---|---|---|---|---|
| 0.1 μg | 4 hr | Plate well-1 | 1.15 | 2.14 | 50.9% |
|  |  | Plate well-2 | 1.12 | 1.89 | 52.6% |
|  | 14 hr | Plate well-1 | 1.10 | 2.29 | 53.9% |
|  |  | Plate well-2 | 1.09 | 2.28 | 53.5% |
|  |  | Tube | 1.07 | 2.10 | 52.7% |
| 1 μg | 4 hr | Plate well-1 | 1.00 | 1.31 | 54.8% |
|  |  | Plate well-2 | 0.96 | 1.78 | 53.0% |
|  |  | Tube | 1.00 | 1.81 | 54.6% |
|  | 14 hr | Plate well-1 | 0.93 | 1.67 | 51.8% |
|  |  | Plate well-2 | 0.98 | 1.67 | 53.2% |
|  |  | Tube | 0.99 | 1.47 | 54.2% |

TABLE 25

Microarray Results for Magnetic Bead-based RNA Amplification and Labeling are Highly Correlated with Existing Methods

| | | | 0.1 μg Total RNA | | | | | | 1 μg Total RNA | | | | | |
| | | | 4 hr | | | 14 hr | | | 4 hr | | | 14 hr | | |
| | | | Plate-1 | Plate-2 | Plate-1 | Plate-2 | Tube | Plate-1 | Plate-2 | Tube | Plate-1 | Plate-2 | Tube |
|---|---|---|---|---|---|---|---|---|---|---|---|---|---|
| 0.1 μg RNA | 4 hr | Plate-1 | 1.000 | 0.998 | 0.991 | 0.991 | 0.992 | 0.987 | 0.992 | 0.985 | 0.990 | 0.988 | 0.986 |
|  |  | Plate-2 |  | 1.000 | 0.991 | 0.992 | 0.993 | 0.989 | 0.993 | 0.987 | 0.992 | 0.990 | 0.989 |
|  | 14 hr | Plate-1 |  |  | 1.000 | 0.998 | 0.997* | 0.991 | 0.993 | 0.993 | 0.992 | 0.995 | 0.993 |
|  |  | Plate-2 |  |  |  | 1.000 | 0.998* | 0.992 | 0.995 | 0.994 | 0.993 | 0.995 | 0.994 |
|  |  | Tube |  |  |  |  | 1.000 | 0.993 | 0.994 | 0.993 | 0.993 | 0.994 | 0.995 |
| 1 μg RNA | 4 hr | Plate-1 |  |  |  |  |  | 1.000 | 0.995 | 0.996* | 0.994 | 0.995 | 0.996 |
|  |  | Plate-2 |  |  |  |  |  |  | 1.000 | 0.997* | 0.998 | 0.997 | 0.995 |
|  |  | Tube |  |  |  |  |  |  |  | 1.000 | 0.996 | 0.997 | 0.995 |
|  | 14 hr | Plate-1 |  |  |  |  |  |  |  |  | 1.000 | 0.997 | 0.995* |
|  |  | Plate-2 |  |  |  |  |  |  |  |  |  | 1.000 | 0.997* |
|  |  | Tube |  |  |  |  |  |  |  |  |  |  | 1.000 |

Key:

Underlined values = well-to-well correlations within one plate;

* = plate-to-tube correlations

Example 30

Combinations of Modified Bead Surfaces Allow More Versatile Nucleic Acid Purification Options It is possible to obtain Dextran magnetic beads with a variety of functionalities. For example, it has been found that some particles from Polysciences, Inc. more efficiently recover dsDNA than do some particles from Micromod. Consequently, a single tube containing both classes of particles can be expected to isolate total nucleic acid (RNA and DNA) more efficiently than one class alone. For example, 100 µl containing 5000 HeLa cells are added to 200 µl of the lysis binding solution (2M GuSCN, 12.5 mM NaCitrate (pH 7.0), 0.25% N Lauryl Sarcosin, 0.05M BME, 50% Isopropanol). A total of 50 µg of ND beads and 50 µg of Dextran beads custom manufactured by Polysciences, Inc. are added as the purification support. After a 2-3 min incubation at 23° C., the magnetic particles are separated with a conventional magnet and the supernatant removed. The bead pellets are successively washed twice with 200 µl of a solution containing 1.3 M GITC, 0.17% N-lauryl sarcosine, 8 mM sodium citrate (pH 7.0), and 33% isopropanol and then further washed twice with 10 mM KCl, 2 mM TrisCl (pH 7.0) and 80% ethanol. The nucleic acid is eluted in 1 mM KCl, 0.2 mM sodium citrate (pH 7.0). The recovery of RNA and DNA can be monitored by spectrophotometry at A260, by fluorescence quantification using the Quant-IT kits for DNA and RNA quantification (Molecular Probes), or by real-time RT-PCR, using RT+ and RT− reactions.

Of course, those of skill in the art, using the teachings of this specification and methods known to them will be able to design or select and obtain, via manufacturing or purchase, a wide variety of particles of use in the invention. Those of skill will further be able to study the functionality of these particles and employ them in appropriate embodiments to the invention to achieve appropriate ends.

Example 31

A Co-Precipitation Assay that Prognosticates Utility when the Co-precipitant is Coupled to a Solid Surface High throughput applications often rely on coated magnetic particles for improved ease of use, greater sample throughput, and reduced variability. Currently, only a few chemistries are widely utilized for the bulk of high throughput nucleic acid purification.

Polymeric co-precipitants can stimulate nucleic acid capture with magnetic beads that non-specifically bind nucleic acid. Polymeric compounds capable of many weak interactions with nucleic acid can facilitate precipitation onto a compatible bead surface, whereas the non-polymeric compounds would be unable to accomplish this co-precipitation, owing to the lack of multiplicity of contacts with the nucleic acid. Similarly effective co-precipitants of RNA and DNA are able to capture those nucleic acids on a solid support, when precipitating conditions are used. The cost and time required to custom manufacture many different bead chemistries, however, can be prohibitive. Therefore, in order to identify an alternative method for testing various potential substrates for RNA binding, an assay was devised that can prognosticate RNA purification with a given surface chemistry, without an obligatory custom synthesis in each case.

A pilot study was performed by comparing polyethylene glycol (formula $(CH_2O)_n$, where n~8000) with the monomer ethylene glycol $C_2H_6O_2$ (n=2) at equivalent concentrations in their abilities to drive RNA onto Dextran-coated magnetic particles. In the presence of high concentrations of salt (1 M), PEG enhanced the purification of 10 µg of mouse liver total RNA (Ambion) over that of the monomer at equivalent concentration. RNA (10 µg/sample), was added to polyethylene glycol at final concentrations of 26.6, 13.3, or 6.6% and 1M NaCl at in a final volume of 135.6 µl. A total of 50 µg of Dextran beads was added and the components were mixed well. The binding reaction was incubated at 23° C. for 10 min followed by incubation on a magnetic stand for 15 min to allow the beads to collect at the bottom of the well. The supernatant was removed and the beads were washed with 200 µl of 80% ETOH. The supernatant from the ethanol wash was removed by suction and samples eluted with 60 µl of dH2O at 70° C. The RNA concentration was quantified by A260 measurements using a NanoDrop spectrophotometer, and confirmed by analysis on an RNA LabChip® using an Agilent 2100 bioanalyzer. The addition of PEG from 5.6 to 22.5 enabled purified RNA yields of greater than >99% whereas even 52% ethylene glycol yielded only 10% of the input RNA. This result indicates that PEG 8000 is able to interact with the RNA and facilitate precipitation on the Dextran particles where the monomer cannot. These data support the notion that long chain polyethylene glycols are effective RNA binding substrates, since the co-precipitation of PEG and RNA suggests a viable interaction between the two. Moreover, the inventors have demonstrates that a PEG-coated surface can capture RNA from solution and act as an effective purification support.

A similar study was performed to compare ficoll 40,000 MW, 70,000 MW and its monomeric equivalent, sucrose. Using the binding conditions described above, ficoll 70K, 40K, and sucrose were tested at 26.6, 13.3 and 6.6% final concentrations. RNA yields are shown in Table 26. For ficoll 40, viscosity at the highest concentration limited the migration of the beads to the magnet and contributed to reduced yields. Compared to the control sample, ficoll 40 was able to bind a maximum of about 74% of the RNA. Sucrose at the same range of concentrations yielded less than 10% that of the best ficoll 40 condition. Thus, RNA binding was most efficient with the polymeric, rather than the monomeric, form of this carbohydrate. Moreover, such polymeric co-precipitants can be used (in combination with salt) as an alternative to alcohols to enable the recovery of nucleic acids on various solid surfaces.

Ficoll 40, ficoll 70, and other ficoll's will have utility in nucleic acid purification if coupled directly to a surface, just as PEG, also an effective nucleic acid co-precipitant, has utility in nucleic acid purification when attached to a solid support.

TABLE 26

Ficoll, but not its Monomeric Equivalent, is an Effective Co-precipitant for the Purification of RNA with Dextran-coated Particles.

| Condition | Yield (%) |
|---|---|
| Ficoll 70 26.6% | 58 |
| Ficoll 70 13.3% | 31 |
| Ficoll 70 6.6% | 0 |
| Ficoll 40 26.6% | 71 |
| Ficoll 40 13.3% | 74 |
| Ficoll 40 6.6% | 47 |
| Sucrose 13.3% | 2 |
| Sucrose 6.6% | 3 |
| NaCl/Isopropanol | 92 |

Example 32

Polyvinylpyrrolidone Enables the Recovery of High Yields of RNA on Dextran-coated Particles Polyvinylpyrrolidone (PVP) is made from the monomer n-vinyl pyrrolidone and is readily available at various molecular weights from chemical suppliers. Using the RNA co-precipitation assay described in Example 31, 10K, 40K, and 360K molecular weight PVP formulations (Sigma) were evaluated. Studies contained 1 M NaCl, 20 μg of RNA, and 50 μg of Dextran-coated magnetic particles. The eluted RNA was quantified by A260, and select samples were also analyzed on an RNA LabChip® using the 2100 Bioanalyzer. For those samples assayed on a LabChip, the quality of the RNA (RNA Integrity Number, or RIN) is also given. Table 27 reveals that all three PVP polymers enabled the recovery of high yields of the input RNA, in the absence of any alcohol. In general, a lower net concentration of PVP was required to achieve the same RNA yield as the polymer length of the PVP was increased. Thus, longer chain PVP molecules presumably provide a greater number of interactions with the RNA during the precipitation step, and less molecules are required to accomplish said precipitation on the bead surface. In addition, it is expected that PVP-10, PVP-40, and PVP-360 will each have utility in nucleic acid purification if coupled directly to a surface, just as PEG, also an effective nucleic acid co-precipitant, has utility in nucleic acid purification when attached to a solid support.

TABLE 27

PVP is an Effective Co-precipitant of RNA.

|  | ng/ul | % Yield | RIN |
|---|---|---|---|
| Control | 291 | 97 |  |
| PEG 26.6% | 279 | 93 |  |
| PEG 13.3% | 308 | 103 | 7.7 |
| PEG 6.6% | 306 | 102 |  |
| PVP 360 10.1% | 188 | 63 | 8 |
| PVP 360 5% | 237 | 79 | 7.9 |
| PVP 360 2.5% | 240 | 80 | 8.1 |
| PVP 40 20.4% | 265 | 88 | 5.1 |
| PVP 40 10.2% | 258 | 86 | 5.3 |
| PVP 40 5.1% | 238 | 79 | 5.3 |
| PVP 10 30.9% | 261 | 87 |  |
| PVP 10 15.4% | 264 | 88 | 7.6 |
| PVP 10 7.7% | 121 | 40 | 7.5 |

Example 33

Polymeric Polyols Enable the Recovery of RNA on Coated Particles

Other polymeric candidates that are expected to have utility in purify RNA or DNA on surfaces include those based on the repeating sugar motif. These include Glycogen, Gum Arabic, Xanthan Gum, Carageenan, Amylose, Agar, Amylopectin, Xylans, beta-Glucans, and many others. This class of compounds is also known as polyols. In a study using 25 μg of input RNA, and 9.5, 4.8, or 2.4% gum arabic (Fluka) in 1.2 M NaCl, ~53% of the input RNA could be purified using 9.5% gum arabic as the co-precipitant (Table 28). These data suggest that the polymer in gum arabic would be useful for binding RNA or DNA when attached to a solid support. More broadly, the inventors anticipate that an polymeric polyol that is an effective nucleic acid co-precipitant will have utility in purifying RNA or DNA when coupled to a solid support.

TABLE 28

Efficiency of RNA Purification with Polymeric Co-precipitants.

| Additive | % Additive | 260/280 | % Yield |
|---|---|---|---|
| PEG 8000 | 23.8 | 2.1 | 94 |
| PEG 8000 | 11.9 | 2.07 | 99 |
| PEG 8000 | 5.9 | 2.08 | 103 |
| Control (NaCl/IP) | 0 | 2.09 | 97 |
| Gum Arabic | 9.5 | 1.98 | 54 |
| Gum Arabic | 4.8 | 1.16 | 0 |
| Gum Arabic | 2.4 | 1.6 | 0 |

Example 34

Identification of Other Useful RNA Purification Chemistries

Twelve different chemical resins were screened for their ability to bind and purify RNA. An Xef RNA transcript was internally labelled with $^{32}$P using Ambion's MEGAScript kit, and spiked into 1 μg of mouse total RNA to a specific activity of 200,000 cpm/ul RNA (20 μl total RNA+2 μl radioactively labelled Xef transcript).

The chemical resins were hydrated to 20% with deionized water. All RNA binding reactions contained: 100 μl RNAqueous lysis buffer (Ambion), 1.1 μl RNA mix (total RNA with Xef tracer), 100 μl solvent (66% or 100% stock concentration). These reagents were mixed, and then 20 μl of 20% resin was added. After a brief incubation, the resins were pelleted at maximum speed in a microfuge. The unbound fraction (supernatant) was removed and the residual radioactivity quantified via scintillation counting. The pellet was washed with 200 ul of RNAqueous wash ⅔ solution (Ambion). The resin was re-pelleted by centrifugation, and the wash removed and counted. For isocyanate, glycerol, and piperidinomethyl resins, bound RNA was eluted with 25 μl of elution buffer (1 mM Tris pH 8.0, 0.1 mM EDTA, 5 mM KCl) at room temperature, and a second elution was performed with the same buffer pre-heated to 95° C. For all other resins, the RNA was eluted in a single step, with a solution pre-heated to 95° C. As shown in Table 29, the results of this screen revealed several chemistries, including phenylsepharose, glycerol(diol), morpholinomethyl, piperidino methyl, and polystyrene aldehyde that recovered RNA with >60% efficiency in at least one solvent condition. The inventors anticipate that such chemistries may prove useful for nucleic acid purification for various applications.

TABLE 29

A Resin Screen to Identifies Chemistries that are Competent to Purify RNA.

| Resin | Solvent | Bound | Unbound | Wash ⅔ | Elution | Total % Recovery |
|---|---|---|---|---|---|---|
| Isocyanate | 33% Acetone | 17109.39 | 3386.03 | 1778.05 | 8408.21 | 41.02482 |
|  | 50% Acetone | 14801.87 | 1537.11 | 3086.22 | 6858.48 | 53.19506 |
|  | 33% EtOH | 17336.96 | 3354.38 | 1783.2 | 4445.51 | 21.48488 |
|  | 50% EtOH | 16168.5 | 4645.74 | 180.03 | 9308.49 | 58.21827 |
|  | 33% Isopropanol | 14204.71 | 5464.12 | 7060.44 | 5095.04 | 25.90413 |

TABLE 29-continued

A Resin Screen to Identifies Chemistries that are Competent to Purify RNA.

| Resin | Solvent | Bound | Unbound | Wash 2/3 | Elution | Total % Recovery |
|---|---|---|---|---|---|---|
| Glycerol(Diol) | 33% Acetone | 18518.67 | 2128.53 | 4886.22 | 9801.45 | 47.47109 |
|  | 50% Acetone | 20172.11 | 354.1 | 123.04 | 12337.65 | 87.20212 |
|  | 33% EtOH | 17839.09 | 4666.58 | 591.2 | 10401.55 | 46.21746 |
|  | 50% EtOH | 17459.73 | 4514.73 | 4478.72 | 8850.42 | 50.17994 |
|  | 33% Isopropanol | 8672.23 | 12388.32 | 1499.64 | 3874.67 | 18.39776 |
| Piperidinomethyl | 33% Acetone | 19373.33 | 1717.82 | 88.04 | 10724.11 | 50.84649 |
|  | 50% Acetone | 20730 | 1020.53 | 252.13 | 11795.16 | 70.34716 |
|  | 33% EtOH | 18110.3 | 3621.05 | 96.05 | 8374.76 | 38.53769 |
|  | 50% EtOH | 17711.86 | 2653.62 | 107.07 | 11063.78 | 71.41815 |
|  | 33% Isopropanol | 14746.54 | 6204.07 | 73.05 | 5428.57 | 25.91127 |
| PolyDMAP | 33% Acetone | 16415.42 | 3150.08 | 32 | 7608.19 | 38.88574 |
|  | 50% Acetone | 15517.09 | 4252.3 | 23 | 6466.45 | 32.70941 |
|  | 33% EtOH | 12329.42 | 7603.87 | 38 | 4147.48 | 20.8068 |
|  | 50% EtOH | 8105.31 | 11844.89 | 22 | 3059.49 | 15.33564 |
|  | 33% Isopropanol | 6040.24 | 13692.8 | 21 | 2625.54 | 13.3053 |
| DIPAM | 33% Acetone | 15703.94 | 3535.88 | 2858.71 | 3510.88 | 18.24799 |
|  | 50% Acetone | 17954.32 | 2434.72 | 558.16 | 4874.44 | 23.90716 |
|  | 33% EtOH | 13660.67 | 6734.29 | 1960.67 | 2069.7 | 10.1481 |
|  | 50% EtOH | 12348.77 | 7593.92 | 137.05 | 2837.09 | 14.22622 |
|  | 33% Isopropanol | 9958.3 | 9730.19 | 212.09 | 3097.33 | 15.73168 |
| Aminomethyl | 33% Acetone | 16966.1 | 3918.86 | 538.26 | 9481.51 | 45.39875 |
|  | 50% Acetone | 18276.55 | 3162.64 | 193.1 | 8108.22 | 37.81962 |
|  | 33% EtOH | 13275.55 | 7219.08 | 965.55 | 4997.83 | 24.38605 |
|  | 50% EtOH | 13091.04 | 8407.13 | 85.05 | 6166.77 | 28.68509 |
|  | 33% Isopropanol | 10215.73 | 10250.72 | 67.04 | 4786.14 | 23.3853 |
| Polystyrene CHO | 33% Acetone | 17803.44 | 2338.06 | 3404.09 | 9961.25 | 49.45635 |
|  | 50% Acetone | 18086.26 | 1863.13 | 278.02 | 12734.89 | 63.83599 |
|  | 33% EtOH | 15718.8 | 4121.47 | 390.04 | 10826.24 | 54.567 |
|  | 50% EtOH | 14849.39 | 4340.69 | 91.01 | 9410.51 | 49.03841 |
|  | 33% Isopropanol | 6950.43 | 11685.39 | 518.11 | 4721.97 | 25.33814 |
| Tris(2-aminomethyl) amine | 33% Acetone | 18245.56 | 2041.51 | 1666.42 | 6102.52 | 30.08083 |
|  | 50% Acetone | 18068.35 | 1995.59 | 1651.49 | 6138.81 | 30.59623 |
|  | 33% EtOH | 15539.3 | 4283.46 | 276.09 | 4147.41 | 20.92246 |
|  | 50% EtOH | 15798.11 | 4034.55 | 220.08 | 5442.09 | 27.44004 |
|  | 33% Isopropanol | 13817.97 | 5613.42 | 207.09 | 4664.01 | 24.00245 |
| Morpholinomethyl | 33% Acetone | 17650.43 | 1932.92 | 231.11 | 13407.37 | 68.46311 |
|  | 50% Acetone | 18751.8 | 1218.63 | 273.14 | 12291.4 | 61.548 |
|  | 33% EtOH | 15096.58 | 4965.81 | 2162.22 | 7087.02 | 35.3249 |
|  | 50% EtOH | 8977.51 | 10408.36 | 1246.76 | 5877.6 | 30.31899 |
|  | 33% Isopropanol | 12096.97 | 6845.49 | 2421.59 | 5655.71 | 29.85732 |
| BOBA | 33% Acetone | 14075.36 | 5582.14 | 35 | 2008.05 | 10.21519 |
|  | 50% Acetone | 14675.03 | 4659.32 | 27 |  |  |
|  | 33% EtOH | 14622.69 | 4068.46 | 42 | 3478.4 |  |
|  | 50% EtOH | 9279.49 | 9878.58 | 33.01 |  |  |
|  | 33% Isopropanol | 14884.06 | 4072.83 | 31.01 |  |  |
| Triphenylphosphine | 33% Acetone | 18128.54 | 2264.56 | 37.01 | 3000.75 |  |
|  | 50% Acetone | 18409.46 | 2128.63 | 61.02 | 11900.51 |  |
|  | 33% EtOH | 17891.11 | 1949.66 | 40.01 | 8230.8 |  |
|  | 50% EtOH | 13766.33 | 5830.24 | 28.01 | 2793.07 |  |
|  | 33% Isopropanol | 16707.23 | 2532.09 | 33.01 | 6846.95 |  |
| Benzylthiomethyl | 33% Acetone | 17712.47 | 2674.27 | 59.03 | 10767.12 |  |
|  | 50% Acetone | 14911.8 | 4812.5 | 84.04 | 1407.73 |  |
|  | 33% EtOH | 17330.86 | 2701.53 | 25.01 | 9490.37 |  |
|  | 50% EtOH | 15009.22 | 5181.16 | 32.02 |  |  |
|  | 33% Isopropanol | 19741.02 | 1321.87 | 28.02 | 4676.07 |  |

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. More specifically, it will be apparent that certain agents that are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

U.S. Pat. No. 4,452,773
U.S. Pat. No. 5,075,430
U.S. Pat. No. 5,234,809
U.S. Pat. No. 5,705,628
U.S. Pat. No. 6,027,945
U.S. Pat. No. 5,545,522

U.S. Pat. No. 6,664,379
U.S. Prov. Appln. 60/155,874
U.S. patent application 2003/0092045
U.S. patent application Ser. No. 10/675,860
Boom et al., *J. Clin. Microbiol.*, 28:495-503, 1990.
Nielsen et al., *Science*, 254:1497, 1991.
Vogelstein and Gillespie, *Proc. Natl. Acad. Sci. USA*, 76:615-619, 1979.
Yamado et al., *J. Virol. Methods*, 27:203-210, 1990.

What is claimed is:

1. A method of separating at least one polynucleotide from a solution containing the polynucleotide, comprising:
admixing magnetic particles having at least one surface comprising a dextran and the solution containing at least one polynucleotide to produce an admixture, wherein the dextran comprises plain dextran or dextran sulfonate;
adjusting a salt concentration and an organic solvent concentration of the admixture to concentrations wherein the at least one polynucleotide binds to the at least one surface to produce a modified surface wherein the organic solvent concentration is a concentration of one or more organic solvents comprising at least one of methanol, ethanol, propanol, isopropanol, butanol, pentanol, a dimethyl sulfoxide, and acetone;
separating the at least one modified surface from the remainder of the admixture while the at least one polynucleotide is bound to the surface; and
contacting the modified surface with an elution buffer, thereby separating the at least one polynucleotide from the at least one surface.

2. The method of claim 1, wherein the salt concentration is a concentration of one or more salts comprising at least one of sodium chloride, magnesium chloride, calcium chloride, potassium chloride, lithium chloride, barium chloride, cesium chloride, sodium perchlorate, guanidinium isothiocyanate, guanidinium hydrochloride, potassium iodide, and sodium iodide.

3. The method of claim 2, wherein the salt concentration is from 0.1M to 5M.

4. The method of claim 2, wherein the salt is guanidinium isothiocyanate.

5. The method of claim 1, wherein the concentration of the organic solvent is adjusted to between about 20% and 50%.

6. The method of claim 1, wherein the polynucleotide solution comprises a lysate of blood, a blood fraction, fresh tissue, fixed tissue, or a cultured cell.

7. The method of claim 1, wherein the polynucleotide is a bacterial polynucleotide or a polynucleotide encoding a bacterial component.

8. The method of claim 1, wherein the polynucleotide is a eukaryotic polynucleotide or a polynucleotide encoding a eukaryotic component.

9. The method of claim 1, wherein the surface is on a magnetic microparticle.

10. The method of claim 9, wherein the separating of the surface is performed using a magnet.

11. The method of claim 1, wherein the at least one polynucleotide bound to the at least one surface is washed with a buffer solution that dissolves one or more impurities bound to the surface while leaving the at least one polynucleotide bound to the at least one surface.

12. The method of claim 1, wherein the at least one polynucleotide is further defined as at least one RNA.

13. The method of claim 12, further defined as comprising binding the at least one RNA bound to the at least one surface in a method comprising using a selective binding solution that does not allow substantial DNA binding to the surface but does allow RNA binding to the surface.

14. The method of claim 12, wherein the RNA bound to the surface is washed with a selective wash solution, wherein the selective wash solution substantially dissolves DNA fragments bound to the surfaces while leaving RNA fragments substantially bound to the surfaces.

15. The method of claim 12, wherein the at least one RNA bound to the at least one surface is eluted with a selective elution solution that elutes the at least one RNA fragment from the surface while leaving DNA fragments substantially bound to the surface.

16. The method of claim 1, wherein the at least one polynucleotide is digested by one or more enzymes while bound to the at least one support.

17. The method of claim 1, wherein the polynucleotide is a viral polynucleotide or a polynucleotide encoding a viral component.

18. The method of claim 1, wherein the solution is a biosample or a lysate of a biosample.

19. The method of claim 1, wherein the solution is an in vitro transcription reaction solution, a reverse transcription reaction solution, a second strand DNA synthesis reaction solution, a DNase reaction solution, a PCR reaction solution, or a RNA amplification reaction solution.

20. The method of claim 1, further comprising performing an RNA amplification reaction, an in vitro transcription reaction, a reverse transcription reaction, a second strand DNA synthesis reaction, a DNase reaction, or a PCR reaction.

21. The method of claim 1, further comprising lysing a cell.

22. The method of claim 1 wherein the at least one surface further comprises polyethyleneglycol.

23. The method of claim 1 wherein the polynucleotide solution comprises frozen tissue.

24. The method of claim 1 wherein the solution containing the polynucleotide is prepared from fixed tissue.

25. The method of claim 1, wherein the polynucleotide is a DNA.

26. The method of claim 1, wherein preparing the solution further comprises conjugating RNA, DNA, or PNA in the solution to a reporter dye.

27. The method of claim 1, further comprising isolating or concentrating RNA, DNA, or PNA.

28. The method of claim 27, further comprising conjugating the RNA, DNA, or PNA to a reporter dye.

29. The method of claim 27, further comprising fragmenting the RNA, DNA, or PNA and then hybridizing at least a portion of the fragmented RNA, DNA, or PNA to a microarray.

30. The method of claim 27, further comprising hybridizing at least a portion of the RNA, DNA, or PNA to a microarray.

31. A method of separating at least one polynucleotide from a solution containing the polynucleotide, comprising:
admixing magnetic particles having at least one surface comprising plain dextran or dextran sulfonate, the solution containing at least one polynucleotide, a salt, and one or more organic solvents to produce an admixture, wherein the salt and organic solvent concentrations of the admixture are such that the at least one polynucleotide binds to the at least one surface to produce a modified surface, wherein the one or more organic solvents comprise at least one of methanol, ethanol, propanol, isopropanol, butanol, pentanol, a dimethyl sulfoxide, and acetone;

separating the at least one modified surface from the remainder of the admixture while the at least one polynucleotide is bound to the surface; and contacting the modified surface with an elution buffer, thereby separating the at least one polynucleotide from the at least one surface.

32. A method of separating at least one polynucleotide from a solution containing the polynucleotide, comprising:

admixing magnetic particles having at least one surface comprising plain dextran or dextran sulfonate, the solution containing at least one polynucleotide, salt, and one or more organic solvents to produce an admixture, wherein the salt and organic solvent concentrations of the admixture are such that the at least one polynucleotide binds to the at least one surface to produce a modified surface, wherein the one or more organic solvents comprise at least one of methanol, ethanol, propanol, isopropanol, butanol, pentanol, a dimethyl sulfoxide, and acetone;

separating the at least one modified surface from the remainder of the admixture while the at least one polynucleotide is bound to the surface; and contacting the modified surface with an elution buffer, thereby separating the at least one polynucleotide from the at least one surface, wherein the salt comprises at least one of sodium chloride, magnesium chloride, calcium chloride, potassium chloride, lithium chloride, barium chloride, cesium chloride, sodium perchlorate, guanidinium isothiocyanate, guanidinium hydrochloride, potassium iodide, and sodium iodide.

* * * * *

UNITED STATES PATENT AND TRADEMARK OFFICE
CERTIFICATE OF CORRECTION

| | | |
|---|---|---|
| PATENT NO. | : 8,426,126 B2 | Page 1 of 1 |
| APPLICATION NO. | : 10/955974 | |
| DATED | : April 23, 2013 | |
| INVENTOR(S) | : Latham et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 524 days.

Signed and Sealed this
Fifth Day of May, 2015

Michelle K. Lee
*Director of the United States Patent and Trademark Office*